(12) United States Patent
Zuo et al.

(10) Patent No.: US 10,738,606 B2
(45) Date of Patent: Aug. 11, 2020

(54) DOWNHOLE REAL-TIME FILTRATE CONTAMINATION MONITORING

(71) Applicant: Schlumberger Technology Corporation, Sugar Land, TX (US)

(72) Inventors: Youxiang Zuo, Burnaby (CA); Kang Wang, Houston, TX (US); Adriaan Gisolf, Bucharest (RO); Ryan Sangjun Lee, Sugar Land, TX (US); Oliver C. Mullins, Houston, TX (US); Shu Pan, Sugar Land, TX (US)

(73) Assignee: SCHLUMBERGER TECHNOLOGY CORPORATION, Sugar Land, TX (US)

( * ) Notice: Subject to any disclaimer, the term of this patent is extended or adjusted under 35 U.S.C. 154(b) by 0 days.

(21) Appl. No.: 16/411,845

(22) Filed: May 14, 2019

(65) Prior Publication Data

US 2019/0264560 A1 Aug. 29, 2019

Related U.S. Application Data

(62) Division of application No. 14/697,382, filed on Apr. 27, 2015, now Pat. No. 10,316,656.

(Continued)

(51) Int. Cl.
*E21B 49/08* (2006.01)
*G01N 33/28* (2006.01)

(52) U.S. Cl.
CPC ....... *E21B 49/088* (2013.01); *G01N 33/2841* (2013.01); *E21B 2049/085* (2013.01)

(58) Field of Classification Search
CPC . E21B 49/088–087; E21B 49/082–081; E21B 2049/085; G01N 33/2841
See application file for complete search history.

(56) References Cited

U.S. PATENT DOCUMENTS

| | | |
|---|---|---|
| 6,274,865 B1 | 8/2001 | Schroer et al. |
| 6,956,204 B2 | 10/2005 | Dong et al. |

(Continued)

OTHER PUBLICATIONS

Zuo et al., A new method for OBM Decontamination in downhole fluid analysis, Mar. 26-28, 2013, International Petroleum Technology Conference, Beijing, China, pp: 1-8.

*Primary Examiner* — Toan M Le
(74) *Attorney, Agent, or Firm* — Trevor G. Grove

(57) ABSTRACT

A method includes identifying linearly behaving data within obtained data associated with fluid obtained from a subterranean formation. Shrinkage factor is determined based on the linearly behaving data. A function relating GOR data of the obtained fluid with the determined shrinkage factor is determined. A first linear relationship between optical density (OD) data of the obtained fluid and the function is determined. A second linear relationship between density data of the obtained fluid and the function is determined. An oil-based mud (OBM) filtrate contamination property of OBM filtrate within the obtained fluid based on the first linear relationship is determined. A native formation property of native formation fluid within the obtained fluid based on the second linear relationship is determined. A volume fraction of OBM filtrate contamination within the obtained fluid based on the OBM filtrate contamination property and the native formation property is estimated.

13 Claims, 21 Drawing Sheets

Related U.S. Application Data

(60) Provisional application No. 62/108,937, filed on Jan. 28, 2015, provisional application No. 61/985,376, filed on Apr. 28, 2014.

(56) References Cited

U.S. PATENT DOCUMENTS

| | | |
|---|---|---|
| 7,711,488 B2 | 5/2010 | Hsu et al. |
| 8,024,125 B2 | 9/2011 | Hsu et al. |
| 8,099,241 B2 | 1/2012 | Niu et al. |
| 8,805,617 B2 | 8/2014 | Zuo et al. |
| 9,557,312 B2 | 1/2017 | Zuo et al. |
| 9,733,389 B2 | 8/2017 | Hsu et al. |
| 2011/0088949 A1* | 4/2011 | Zuo .................... E21B 49/08 175/48 |
| 2014/0316705 A1 | 10/2014 | Zuo et al. |
| 2014/0360257 A1 | 12/2014 | Indo et al. |
| 2015/0135814 A1 | 5/2015 | Zuo et al. |
| 2015/0142317 A1 | 5/2015 | Zuo et al. |
| 2015/0211361 A1 | 7/2015 | Gisolf et al. |
| 2015/0292324 A1 | 10/2015 | Jackson et al. |
| 2015/0308261 A1 | 10/2015 | Zuo et al. |
| 2015/0308264 A1 | 10/2015 | Zuo et al. |
| 2016/0061743 A1 | 3/2016 | Wang et al. |
| 2016/0130940 A1 | 5/2016 | Hsu et al. |
| 2016/0131630 A1 | 5/2016 | Zuo et al. |
| 2016/0186559 A1 | 6/2016 | Wang et al. |
| 2016/0186560 A1 | 6/2016 | Zuo et al. |
| 2016/0208600 A1 | 7/2016 | Gisolf et al. |
| 2017/0247997 A1 | 8/2017 | Kovalevsky |

* cited by examiner

DOWNHOLE REAL-TIME FILTRATE CONTAMINATION MONITORING

CROSS-REFERENCE TO RELATED APPLICATIONS

This application is the Divisional of earlier filed U.S. Non-Provisional application Ser. No. 14/697,382, filed Apr. 27, 2015 which claims priority to and the benefit of U.S. Provisional Application No. 61/985,376, entitled "Downhole Real-Time Filtrate Contamination Monitoring," filed Apr. 28, 2014, and also claims priority to and the benefit of U.S. Provisional Application No. 62/108,937, entitled "Formation Volume Factor and API Gravity Log Downhole in Real-Time," filed Jan. 28, 2015, the entire disclosures of which are hereby incorporated herein by reference.

BACKGROUND OF THE DISCLOSURE

The present disclosure pertains to downhole oil-based mud (OBM) filtrate contamination monitoring (OCM) in real time. A known OCM approach utilizes an optical density mixing rule in which both optical density endpoints of a pure OBM filtrate and a pure native formation fluid are known. However, existing OCM is limited with respect to high gas-oil ratio (GOR) fluids, such as volatile oils and gas condensates, and for formation fluids with little to no optical density contrast relative to OBM filtrate.

SUMMARY OF THE DISCLOSURE

This summary is provided to introduce a selection of concepts that are further described below in the detailed description. This summary is not intended to identify indispensable features of the claimed subject matter, nor is it intended for use as an aid in limiting the scope of the claimed subject matter.

The present disclosure introduces a method that includes identifying linearly behaving data within obtained data associated with fluid obtained from a subterranean formation. Shrinkage factor is determined based on the linearly behaving data. A function relating GOR data of the obtained fluid with the determined shrinkage factor is determined. A first linear relationship between optical density (OD) data of the obtained fluid and the function is determined. A second linear relationship between density data of the obtained fluid and the function is determined. An oil-based mud (OBM) filtrate contamination property of OBM filtrate within the obtained fluid based on the first linear relationship is determined. A native formation property of native formation fluid within the obtained fluid based on the second linear relationship is determined. A volume fraction of OBM filtrate contamination within the obtained fluid based on the OBM filtrate contamination property and the native formation property is estimated.

The present disclosure also introduces a method that includes a stock tank oil (STO) basis density of a fluid obtained from a subterranean formation based on data associated with the obtained fluid. The data includes gas-oil ratio (GOR) data. The estimated STO-basis density of the obtained fluid is fitted as a function of the GOR data to determine an STO-basis density of oil-based mud (OBM) filtrate contamination in the obtained fluid and a parameter relating the STO-basis density of the obtained fluid, the STO-basis density of the OBM filtrate contamination, and the GOR data. The STO-basis density of the obtained fluid is determined based on the determined STO-basis density of the OBM filtrate contamination, the parameter, and the GOR data, thus obtaining a log of the STO-basis density of the obtained fluid with respect to volume of the obtained fluid or time elapsed during obtaining the obtained fluid. An API gravity log is determined based on the log of the STO-basis density of the obtained fluid. A volume fraction of OBM filtrate contamination within the obtained fluid based on the API gravity log is estimated.

The present disclosure also introduces a method that includes determining a linear relation between formation volume factor (FVF) data of a fluid obtained from a subterranean formation and gas-oil ratio (GOR) data of the fluid. Data associated with the obtained fluid includes the FVF data and GOR data. Stock tank oil (STO) basis density of native formation fluid within the obtained fluid is determined based on a slope of the linear relation, a GOR of the native formation fluid, and a density of the native formation fluid. A parameter is then determined, relating STO-basis density of the native formation fluid, STO-basis density of oil-based mud (OBM) filtrate contamination within the obtained fluid, and GOR of the native formation fluid. STO-basis density of the obtained fluid is determined based on the STO-basis density of OBM filtrate contamination, the parameter, and the GOR data.

These and additional aspects of the present disclosure are set forth in the description that follows, and/or may be learned by a person having ordinary skill in the art by reading the materials herein and/or practicing the principles described herein. At least some aspects of the present disclosure may be achieved via means recited in the attached claims.

BRIEF DESCRIPTION OF THE DRAWINGS

The present disclosure is understood from the following detailed description when read with the accompanying figures. It is emphasized that, in accordance with the standard practice in the industry, various features are not drawn to scale. In fact, the dimensions of the various features may be arbitrarily increased or reduced for clarity of discussion.

DETAILED DESCRIPTION

Figure 1:
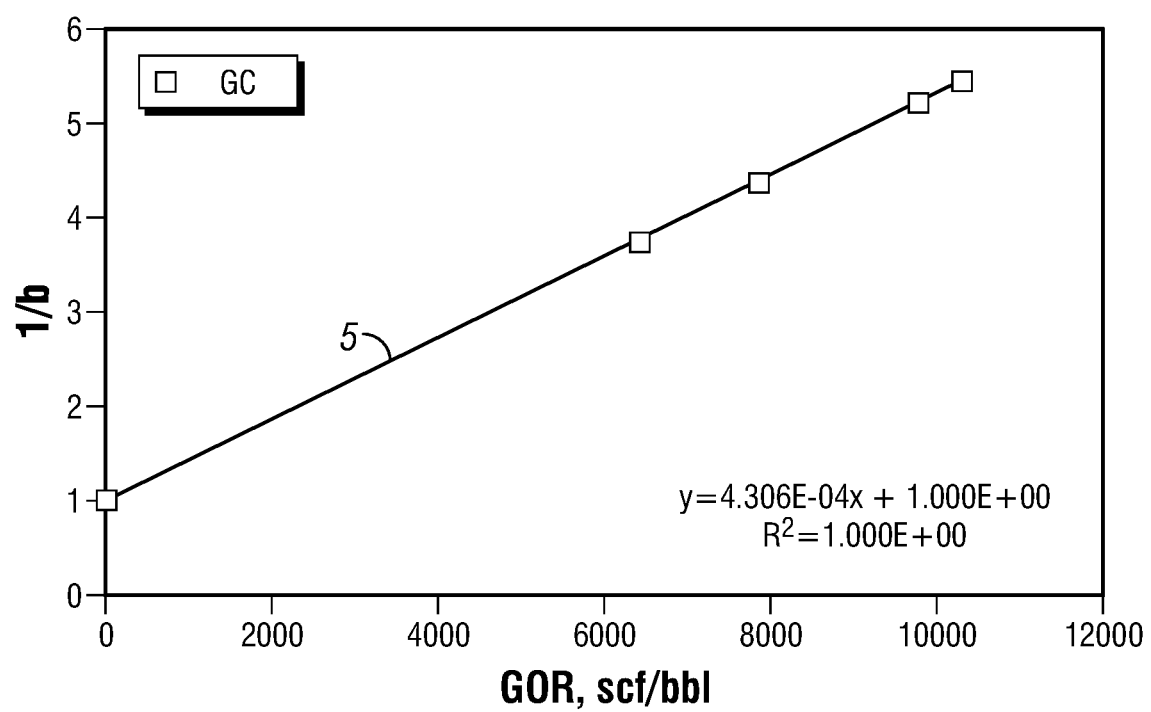
FIG. 1 is a graph depicting one or more aspects of the present disclosure.

It is to be understood that the following disclosure provides many different embodiments, or examples, for implementing different features of various embodiments. Specific examples of components and arrangements are described below to simplify the present disclosure. These are, of course, merely examples and are not intended to be limiting. In addition, the present disclosure may repeat reference numerals and/or letters in the various examples. This repetition is for the purpose of simplicity and clarity and does not in itself dictate a relationship between the various embodiments and/or configurations discussed. Moreover, the formation of a first feature over or on a second feature in the description that follows may include embodiments in which the first and second features are formed in direct contact, and may also include embodiments in which additional features may be formed interposing the first and second features, such that the first and second features may not be in direct contact.

OCM may be utilized in conjunction with multiple fluid properties, such as GOR, density, optical density (OD), and composition, among others. For example, existing methods may fit GOR directly with OBM contamination utilizing a power function to obtain GOR values for the native formation fluid and the OBM filtrate contamination. However, while the obtained OBM filtrate contamination is on a stock tank oil (STO) basis, it is often treated equivalent to that on the live fluid basis. This can result in a large error for high GOR fluids. Because formation volume factor (FVF, the reciprocal of the shrinkage factor) is far away from unity for high GOR fluids, FVF (or shrinkage factor) varies from approximately one (corresponding to the pure OBM filtrate) to a large number during cleanup. This is exhibited in the example laboratory data shown in FIG. 1, which depicts the linear variation 5 of FVF (1/b) relative to GOR of a known gas condensate during a simulated cleanup process, where GOR=0 corresponds to pure OBM filtrate, and GOR=$GOR_0$ corresponds to native formation fluid. The large change in FVF during cleanup renders a linear relationship between GOR and density (and/or OD) invalid for high GOR fluids over an entire OBM filtrate contamination range.

Figure 2:
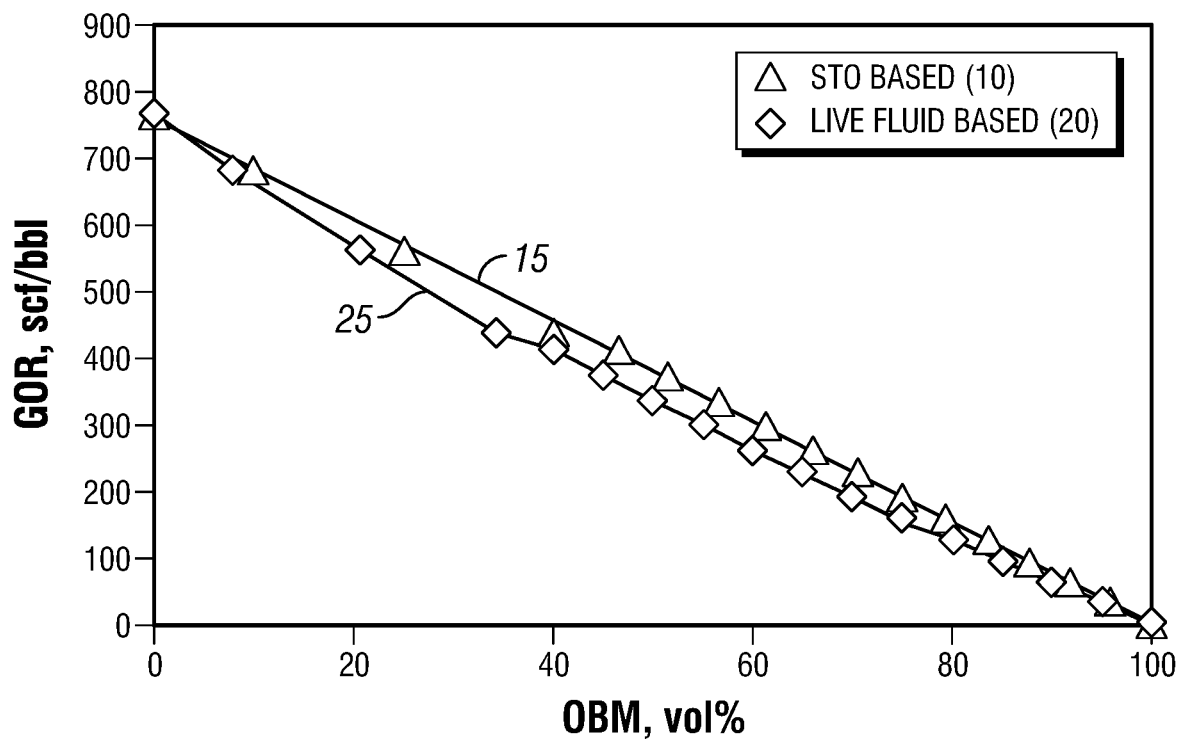
FIG. 2 is a graph depicting one or more aspects of the present disclosure.
Figure 3:
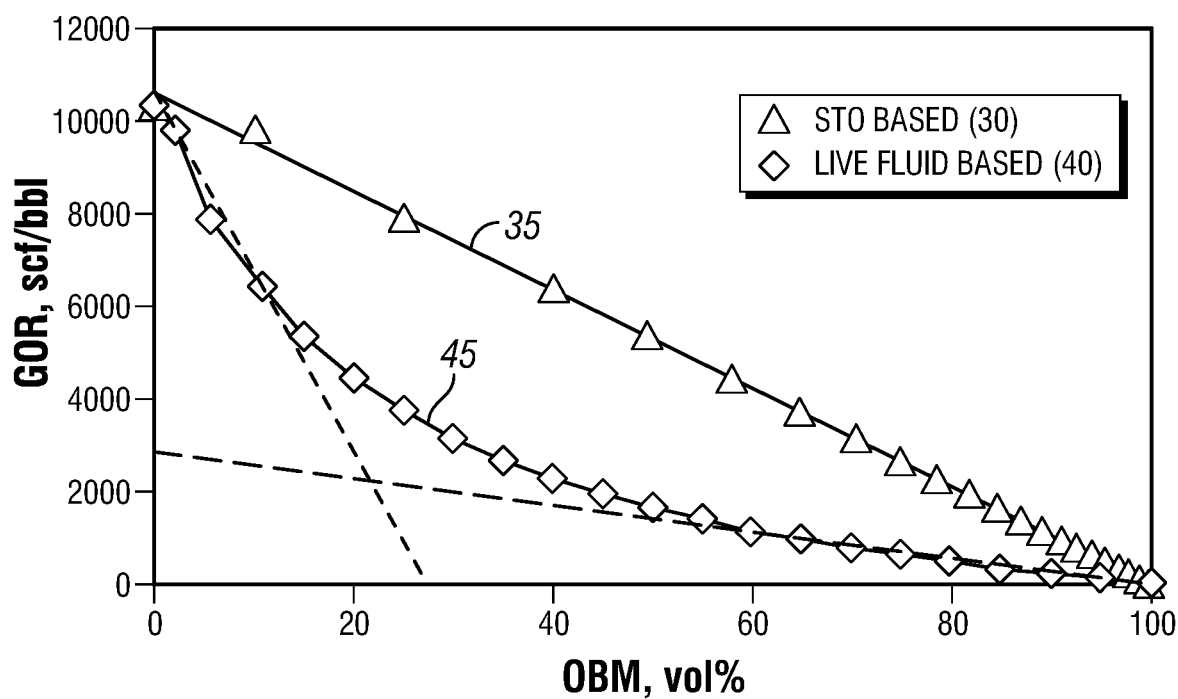
FIG. 3 is a graph depicting one or more aspects of the present disclosure.

For example, FIG. 2 illustrates GOR variations as a function of OBM volume percentage for an example black oil, and FIG. 3 illustrates GOR variations as a function of OBM volume percentage for an example gas condensate. In FIG. 2, STO based data 10 for the example black oil reflects a linear relationship 15 between GOR and OBM volume percentage for the entire contamination range (0-100%), while live fluid based data 20 for the example black oil reflects a non-linear relationship 25 between GOR and OBM volume percentage. Similarly, in FIG. 3, STO based data 30 for the example gas condensate reflects a linear relationship 35 between GOR and OBM volume percentage for the entire contamination range (0-100%), while live fluid based data 40 for the example gas condensate reflects a non-linear relationship 45 between GOR and OBM volume percentage. FIGS. 2 and 3 demonstrate that large errors may occur if a linear relationship between GOR and other fluid properties is utilized to extrapolate those other properties to native formation fluid and pure OBM filtrate, when GOR is not corrected for shrinkage.

Figure 4:
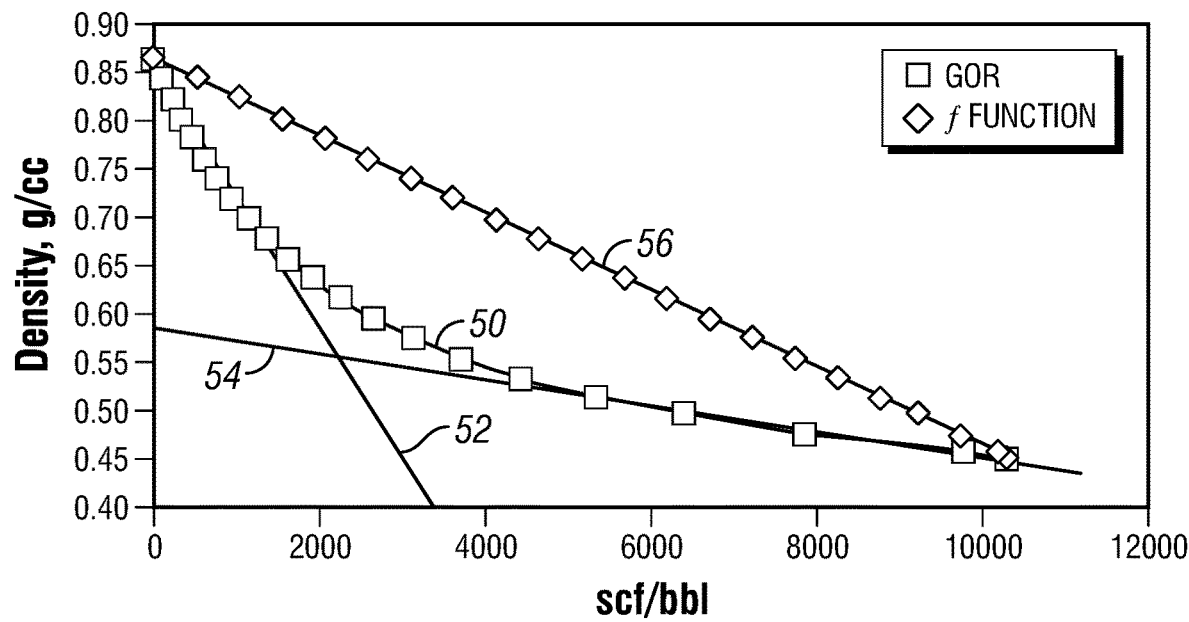
FIG. 4 is a graph depicting one or more aspects of the present disclosure.

Such errors are further demonstrated in FIG. 4, which depicts a relationship 50 between density and GOR for an example gas condensate. That is, one can linearize the early time cleanup data (in the low GOR and high OBM filtrate contamination range) and show that an extrapolation 52 to $GOR_0$ (native formation fluid) results in a large error. In FIG. 4, the extrapolation 52 to $GOR_0$ indicates a $GOR_0$ of about 3350 scf/bbl, substantially less than the true GOR that is greater than 10,000 scf/bbl. Similarly, when linearizing using late time cleanup data (in the high GOR and low OBM filtrate contamination range), an extrapolation 54 to zero GOR (pure OBM filtrate) also leads to a large error. In FIG. 4, the extrapolation 54 to zero GOR indicates a density of about 0.58 g/cc, substantially less than the true density of about 0.88 g/cc.

However, as also shown in FIG. 4, a linear relationship 56 can be obtained between density and an auxiliary function $f=[GOR_0-(GOR_0-GOR)b]$, referred to as the $f$ function. Further details about the $f$ function are described below.

It is also noted that existing OD multi-channel OCM processing mandates that measured fluids have sufficient OD contrast in the reference channel. However, if the OD contrast in the reference channel is not sufficient, the processing is inaccurate. One or more aspects of the present disclosure, however, pertain to methods that determine properties of the native formation fluid and OBM filtrate for low and high GOR fluids (and other kinds of formation fluids).

Live fluid based OBM filtrate contamination in volume fraction ($v_{obm}$) can be expressed in different ways according to different sensors. For example, Equation (1) set forth below (derived from the Beer-Lambert law) is applicable to optical sensors.

$$v_{obm} = \frac{OD_{0i} - OD_i}{OD_{0i} - OD_{obmi}} \tag{1}$$

where, for channel i, $OD_{0i}$ is the optical density of the native formation fluid, $OD_i$ is the optical density of the contaminated fluid obtained by a downhole fluid analysis (DFA) tool (referred to as apparent optical density), and $OD_{obmi}$ is the optical density of the OBM filtrate.

Similarly, Equation (2) set forth below is applicable to density sensors.

$$v_{obm} = \frac{\rho_0 - \rho}{\rho_0 - \rho_{obm}} \tag{2}$$

where $\rho_0$ is the density of the native formation fluid, $\rho$ is the density of the contaminated fluid obtained by the DFA tool (referred to as apparent density), and $\rho_{obm}$ is the density of the pure OBM filtrate.

Similarly, Equation (3) set forth below is applicable to GOR.

$$v_{obm} = bv_{obmSTO} = b\frac{GOR_0 - GOR}{GOR_0}, b = \frac{B_{OBM}}{B_o} \tag{3}$$

where $GOR_0$ is the gas/oil ratio of the native formation fluid and GOR is the gas/oil ratio of the contaminated fluid obtained by the DFA tool (referred to as apparent GOR).

Apparent GOR can be obtained from DFA measurements at a series of times during cleanup. The OBM filtrate contamination level in volume fraction based on stock tank oil ($v_{obmSTO}$) can be converted to that based on the live fluid at downhole conditions by the shrinkage factor b.

The formation volume factor ($B_o$) of the formation fluid is defined as the ratio of the volume (V) of the formation fluid at formation conditions to the volume of stock tank oil at standard conditions ($V_{STOStd}$), as set forth below in Equation (4).

$$B_o = \frac{V}{V_{STOStd}} = \left(\frac{\rho_{STOStd}}{\rho}\right)\left(1 + \frac{GOR}{\rho_{STOStd}}\frac{M_{gas}P_{Std}}{RT_{Std}}\right) = \left(\frac{\rho_{STOStd}}{\rho}\right)\left(1 + \frac{GORM_{gas}}{23.69\rho_{STOStd}}\right) \tag{4}$$

where $\rho_{STOStd}$ is the density of STO at standard conditions and $M_{gas}$ is the gas molecular weight at standard conditions. $P_{Std}$ and $T_{Std}$ are the pressure and temperature of standard conditions (14.7 psi and 60 degrees F.), and R is the gas constant, which is 23.69 based on SI units.

Apparent GOR and density may be measured by DFA and/or obtained from such measurements. The gas molecular weight $M_{gas}$ may be calculated according to composition data, which may also be determined via DFA.

An artificial neural network (ANN) that is utilized in existing DFA GOR algorithms may be utilized to estimate $\rho_{STOStd}$. However, if $\rho_{STOStd}$ determined via ANN processing is not sufficiently accurate, one can assume that $\rho_{STOStd}$ is approximately constant if densities of the OBM filtrate and formation fluid at standard conditions are sufficiently similar. OBM filtrate contamination may also or instead be based on STO, such as via utilization of Equation (5) set forth below.

$$v_{obmSTO} = \frac{\rho_{0STOStd} - \rho_{STOStd}}{\rho_{0STOStd} - \rho_{obmStd}} = \frac{(GOR_0 - GOR)}{GOR_0} \tag{5}$$

Accordingly, $\rho_{STOStd}$ is linearly related to GOR. This may be utilized as set forth below in Equation (6).

$$\rho_{STOStd} = \rho_{obmStd} - \frac{\rho_{0STO} - \rho_{obmStd}}{GOR_0}GOR \tag{6}$$

Equation (6) utilizes OBM filtrate density at standard conditions. One can assume that the density of OBM filtrate at standard conditions ($\rho_{obmStd}$) is approximately equal to that at flowline conditions ($\rho_{obm}$) if an extrapolation method is utilized to obtain $\rho_{obm}$. One can also calculate $\rho_{obmStd}$ and $\rho_{obm}$ utilizing correlations according to different types of OBM, such as may include diesel, mineral oils, and/or synthetic-based muds (e.g., n-paraffins, olefins, and/or esters). The densities of these OBMs may be measured by a PVT laboratory and/or obtained from publicly available literature. The ranges of temperatures and pressures may cover various formation and standard conditions. The experimental density measurements may then be correlated by the polynomial function of temperature (degrees F.) and pressure (psia) set forth below in Equation (7).

$$\rho_{obm} = \sum_{i=0}^{2}\sum_{j=0}^{1} a_{ij}P^i T^j \tag{7}$$

where each $a_{ij}$ is a coefficient of the polynomial function, regressed by matching the experimental density data for different OBM. The $\rho_{obmStd}$ may also be obtained utilizing a recent DFA station, or previous wells if the same type of OBM is utilized. The $\rho_{STOStd}$ may then be populated according to GOR utilizing Equation (6) if $GOR_0$ and $\rho_{0STOStd}$ or $\rho_{STOStd}$ are known for a corresponding GOR.

The formation volume factor of the OBM filtrate $B_{oobm}$ is defined as the ratio of the volume of the OBM filtrate at formation conditions $V_{obm}$ to the volume at standard conditions $V_{obmStd}$, as set forth below in Equation (8).

$$B_{oobm} = \frac{V_{obm}}{V_{obmStd}} = \frac{\rho_{obmStd}}{\rho_{obm}} \tag{8}$$

$B_{oobm}$ is approximately equal to unity, resulting in Equation (9) set forth below.

$$\frac{1}{b} = \left(\frac{\rho_{obm}}{\rho_{obmStd}}\right)\left(\frac{\rho_{STOStd}}{\rho}\right)\left(1 + \frac{GORM_{gas}}{23.69\rho_{STOStd}}\right) \quad (9)$$

It is noted that when GOR=0 (pure OBM filtrate), $\rho_{STOStd} = \rho_{obmStd}$ and $\rho = \rho_{obm}$. Thus, b=1.

Also, Equation (10), set forth below, applies when GOR=$GOR_0$.

$$\frac{1}{b_0} = \left(\frac{\rho_{obmStd}}{\rho_{obm}}\right)\left(\frac{\rho_{0Std}}{\rho_0}\right)\left(1 + \frac{GOR_0 M_{gas}}{23.69\rho_0}\right) \quad (10)$$

Once $GOR_0$ is obtained, $b_0$ may be determined utilizing Equation (10).

The formation volume factor and/or shrinkage factor may also be determined in other ways within the scope of the present disclosure.

OBM filtrate contamination in volume fraction based on live fluid may be expressed as set forth below in Equation (11).

$$v_{obm} = \frac{OD_{0i} - OD_i}{OD_{0i} - OD_{obmi}} = \frac{\rho_0 - \rho}{\rho_0 - \rho_{obm}} = \frac{(GOR_0 - GOR)b}{(GOR_0)} \quad (11)$$

For the given formation fluid and OBM filtrate, properties of the native formation fluid and pure OBM filtrate are constant, including $OD_{0i}$, $OD_{obmi}$, $\rho_0$, $\rho_{obm}$, and $GOR_0$. Therefore, from Equation (11), the relationships among $OD_i$, $\rho$, and $(GOR_0-GOR)b$ are linear. Thus, one may consider the auxiliary function g set forth below in Equation (12), which is referred to as the g function.

$$g = (GOR_0 - GOR)b \quad (12)$$

When g=0, GOR=$GOR_0$. Thus, the g function may be fit utilizing a power function instead of GOR itself, which may provide more consistent results when GOR is obtained from data from multiple sensors.

If a power function is utilized to fit the cleanup data, such as may comprise an array of OD, density, and GOR relative to pumped volume or pumping time, one may utilize Equation (13) set forth below.

$$v_{obm} = \frac{OD_{0i} - OD_i}{OD_{0i} - OD_{obmi}} = \frac{\rho_0 - \rho}{\rho_0 - \rho_{obm}} = \frac{g}{GOR_0} = \beta V^{-\gamma} \quad (13)$$

where V is the pumped volume, which can be replaced by pumping time t, and β and γ are adjustable fitting parameters. When pumped volume or pumping time approaches infinity, $v_{obm}$ approaches zero, corresponding to the pure native formation fluid.

Rearrangement of the above relations results in Equations (14), (15), (16), and (16A), set forth below.

$$OD_{0i} - OD_i = (OD_{0i} - OD_{obmi})\beta V^{-\gamma} = \beta_{1i} V^{-\gamma} \quad (14)$$

$$\rho_0 - \rho = (\rho_0 - \rho_{obm})\beta V^{-\gamma} = \beta_2 V^{-\gamma} \quad (15)$$

$$g = (GOR_0 - GOR)b = GOR_0 \beta V^{-\gamma} = \beta_3 V^{-\gamma} \quad (16)$$

$$GOR_0 - f = g = GOR_0 \beta V^{-\gamma} = \beta_3 V^{-\gamma} \quad (16A)$$

where $f$ is $GOR_0 - (GOR_0 - GOR)b$, referred to as the $f$ function.

It is noted that the fitting exponent "−γ" may be kept the same for OD, density, and GOR fitting, which may make fitting more robust and/or reliable.

Taking the logarithm on both sides of Equations (14)-(16A) results in Equations (17), (18), (19), (19A), and (19B), set forth below.

$$\ln|OD_{0i} - OD_i| = -\gamma \ln V + \ln \beta_{1i} \quad (17)$$

$$\ln|\rho_0 - \rho| = -\gamma \ln V + \ln \beta_2 \quad (18)$$

$$\ln|(GOR_0 - GOR)b| = -\gamma \ln V + \ln \beta_3 \quad (19)$$

$$\ln|g| = -\gamma \ln V + \ln \beta_3 \quad (19A)$$

$$\ln|(GOR_0 - f)| = -\gamma \ln V + \ln \beta_3 \quad (19B)$$

Hence, in log-log plots, one can obtain a linear relation in a selected interval of pumped volume or pumping time, such that the slope is γ.

Figure 5:
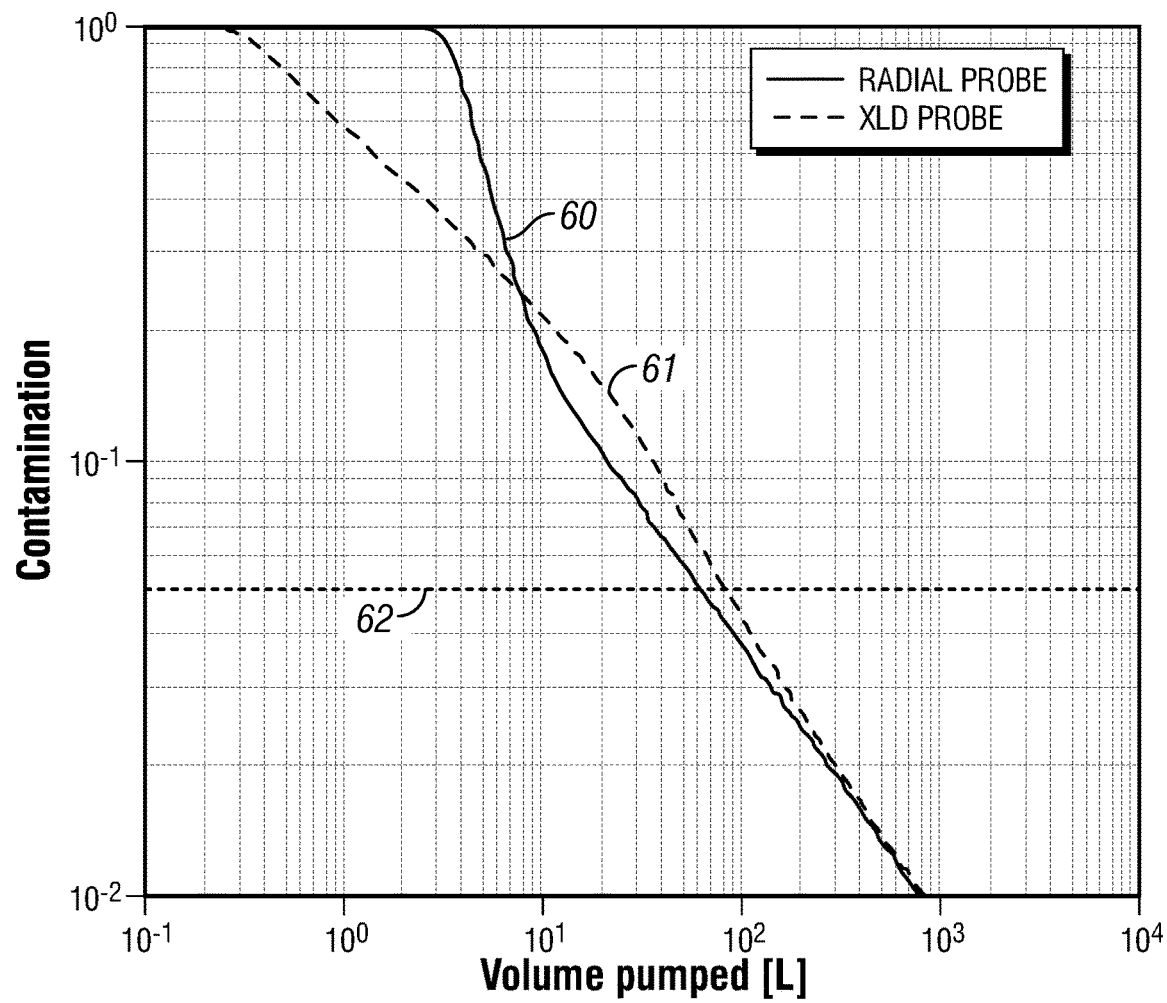
FIG. 5 is a graph depicting one or more aspects of the present disclosure.
Figure 6:
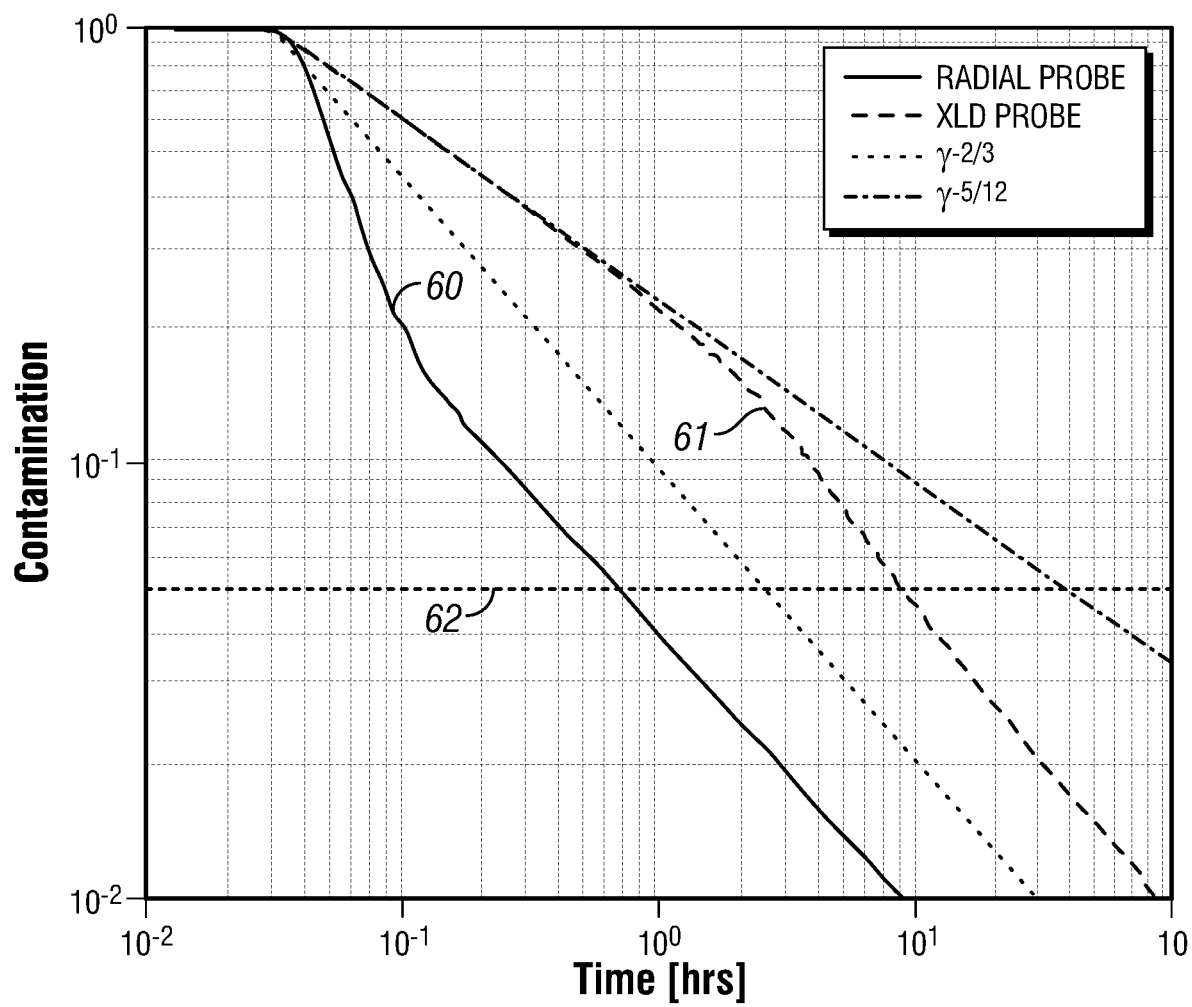
FIG. 6 is a graph depicting one or more aspects of the present disclosure.

FIGS. 5 and 6 depict example contamination cleanup curves for OBM filtrate cleanup during oil sampling utilizing a radial unfocused sampling probe (solid line 60) and an extra-large diameter unfocused sampling probe (dashed line 61), including example contamination cleanup versus pumped volume (FIG. 5) and pumping time (FIG. 6). Unfocused sampling probes have, at a minimum, a single inlet flowline connecting one or more probe inlets to the internal hydraulic circuitry of the downhole tool, whereas focused sampling probes have two inlet flowlines (sample and guard) connecting the corresponding sample and guard inlets of the probe to the internal hydraulic circuitry of the downhole tool. Contamination in FIGS. 5 and 6 is plotted as a volume fraction (0=pure oil; 1=pure filtrate). FIGS. 5 and 6 also include a dotted line 62 demarking a contamination level of five percent.

To perform the fitting, if a radial unfocused sampling probe is utilized, the slope γ may initially be set at ⅔ (0.667) when $v_{obm}$ is less than about ten percent, such as when late time cleanup data is utilized. If an unfocused single probe is utilized, the slope γ may initially be set at 5/12, at least during early time cleanup. However, if $v_{obm}$ is less than about three percent (among other examples within the scope of the present disclosure), such as during late time cleanup, setting the slope γ at ⅔ may obtain more reliable results for end points of the native formation fluid, as shown in FIGS. 5 and 6. However, other initial values for γ are also within the scope of the present disclosure. The log-log plot may also give a visual view of the fitting results in the selected interval, as shown in FIGS. 5 and 6.

Figure 7:
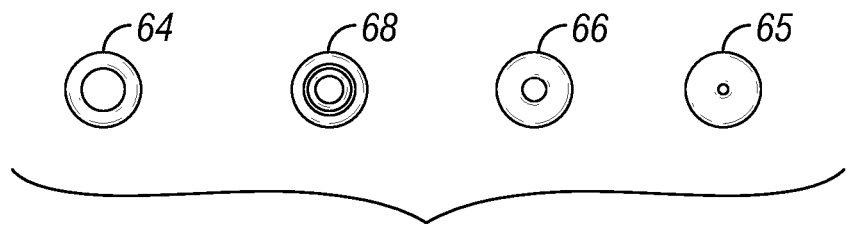
FIG. 7 is a schematic view of at least a portion of apparatus according to one or more aspects of the present disclosure.

FIG. 7 schematically depicts an extra-large diameter unfocused sampling probe 64, such as may correspond to line 62 in FIGS. 5 and 6, and several other sampling probes that may be utilized according to one or more aspects of the present disclosure. The extra-large diameter unfocused sampling probe 64 may have a surface flow area of about 2.01 in². Other unfocused sampling probes depicted in FIG. 7 include a standard sampling probe 65 that may have a surface flow area of about 0.15 in², and a large diameter sampling probe 66 that may have a surface flow area of about 0.85 in². One or more aspects of the present disclosure may also be utilized in conjunction with a focused sampling probe 68, such as may have a total (sample plus guard) surface flow area of about 1.01 in². However, the sampling probes 64-66 and 68 depicted in FIG. 7 are merely examples, and other focused and unfocused sampling probes having other surface flow areas are also within the scope of the present disclosure.

Figure 8:
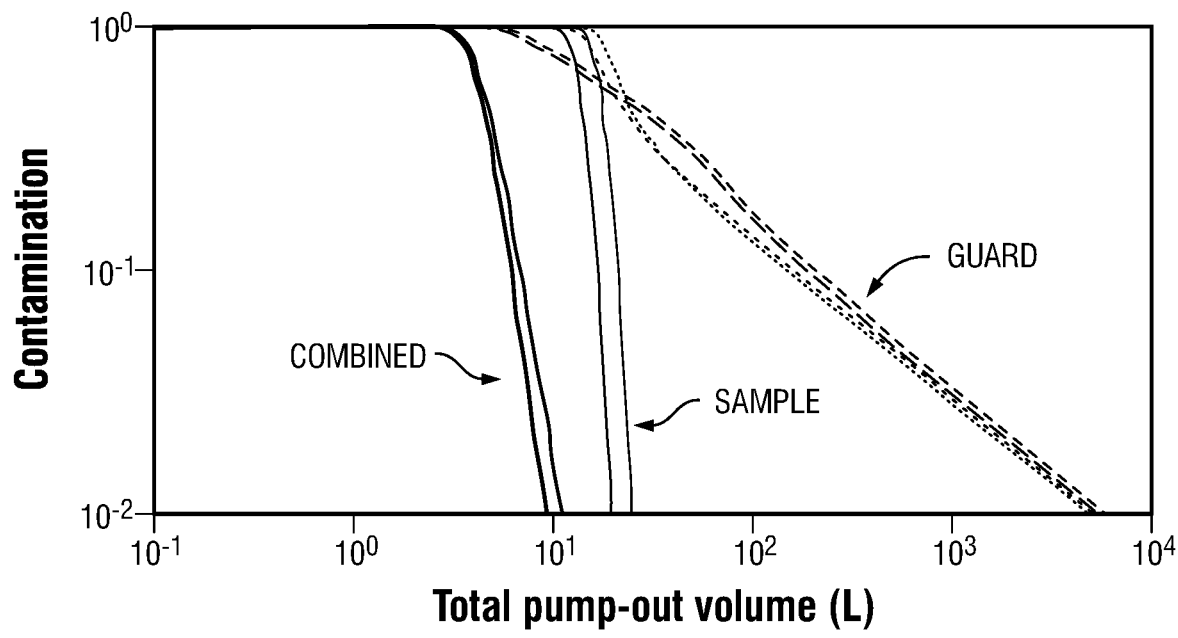
FIG. 8 is a graph depicting one or more aspects of the present disclosure.
Figure 9:
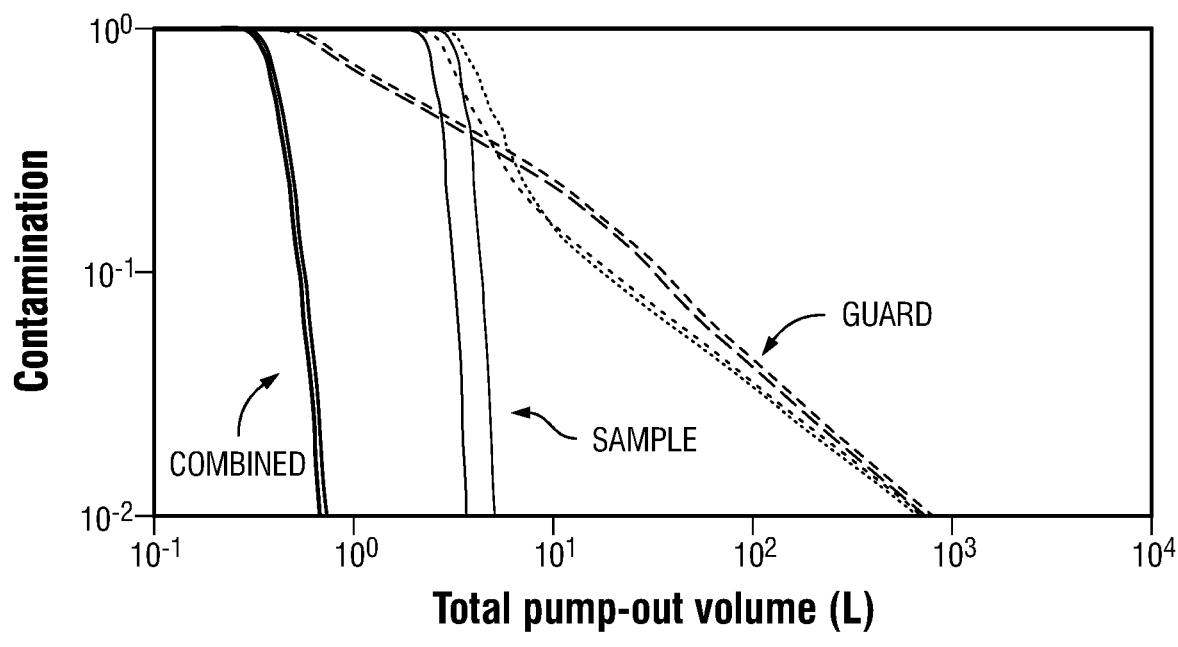
FIG. 9 is a graph depicting one or more aspects of the present disclosure.

FIG. 8 depicts example contamination cleanup curves for a radial focused sampling probe, and FIG. 9 depicts example contamination cleanup curves for a focused sampling probe, such as the focused sampling probe 68 shown in FIG. 7. As shown in FIGS. 8 and 9, when a focused sampling probe is utilized, the fluid in the guard flowline (dashed curves) has similar behavior to fluid obtained with an unfocused single sampling probe, and the fluid in the guard line of the radial focused sampling probe has similar behavior to fluid obtained with a radial unfocused sampling probe. The late time guard flowline may thus correspond to a slope $\gamma$ of $\frac{2}{3}$. FIGS. 8 and 9 also depict that when the fluid in the sample flowline (solid curves) reaches low contamination, and there is an approximate linear relation between $v_{obm}$ and V (or t) for the sample flowline in the log-log plot, the fluid in the guard flowline (dashed curves) still has very high OBM filtrate contamination. Thus, the sample flowline cleanup data may be utilized for the power function fitting, and the slope $\gamma$ may be treated as an adjustable parameter. For example, the slope $\gamma$ may be much greater than $\frac{2}{3}$.

It is noted that an increase in the value of the slope $\gamma$ indicates a faster decrease in $v_{obm}$ (faster cleanup). Thus, the smaller the value of the slope $\gamma$, the more conservative the $v_{obm}$ estimation (the bigger $v_{obm}$).

Figure 10:
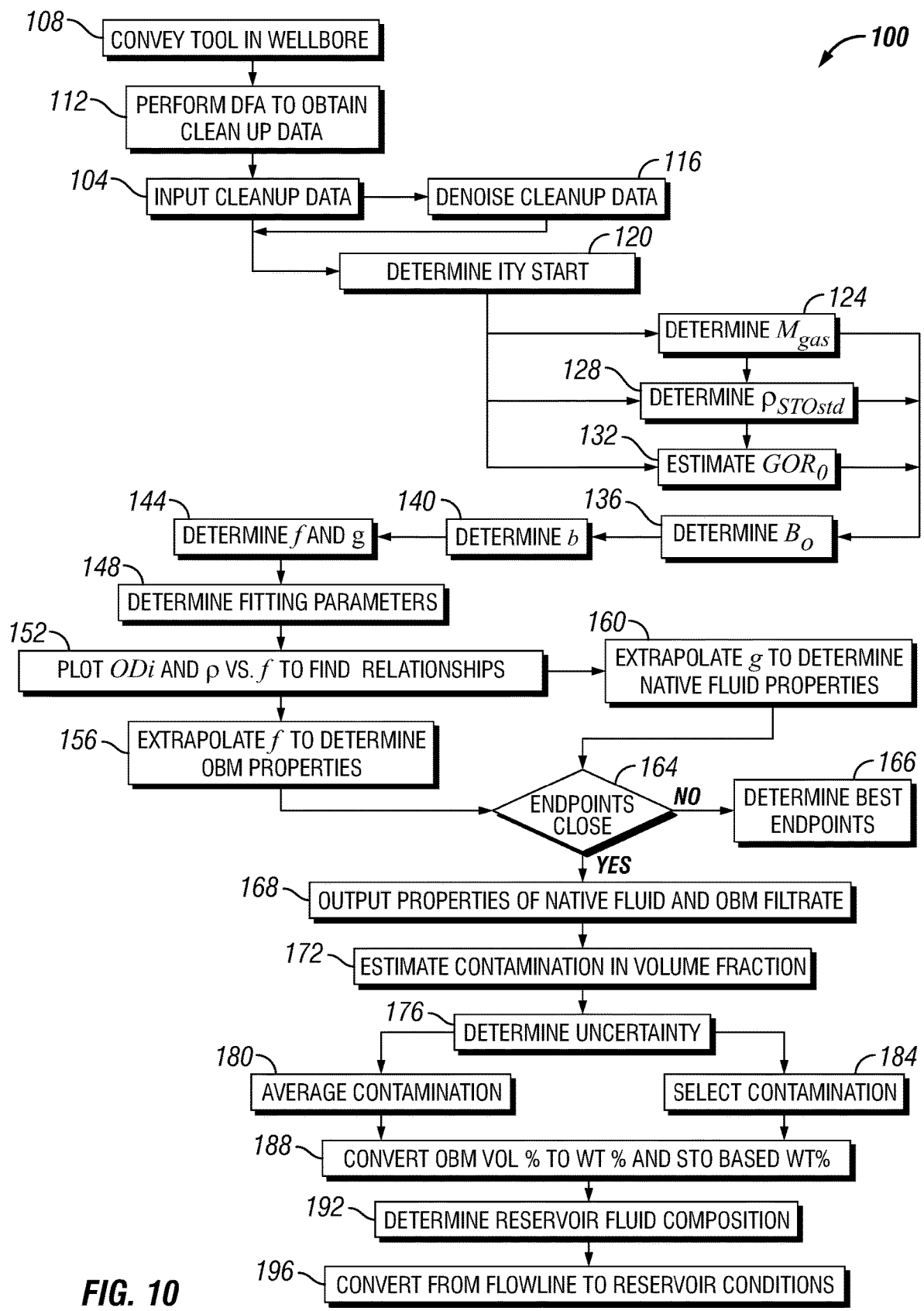
FIG. 10 is a flow-chart diagram of at least a portion of a method according to one or more aspects of the present disclosure.

FIG. 10 is a flow-chart diagram of at least a portion of a method (100) depicting a generalized workflow for OCM according to one or more aspects of the present disclosure. The method (100) includes inputting (104) fluid parameters and other cleanup data obtained DFA utilizing a downhole sampling tool. The method (100) may also include conveying (108) the downhole sampling tool in a wellbore to a subterranean formation penetrated by the wellbore, and operating (112) the downhole sampling tool and/or surface equipment in communication with the downhole sampling tool to obtain the cleanup data. The downhole sampling tool and/or surface equipment may then perform the cleanup data input (104) and/or the following actions, whether autonomously or in conjunction with a human operator's actions.

Figure 11:
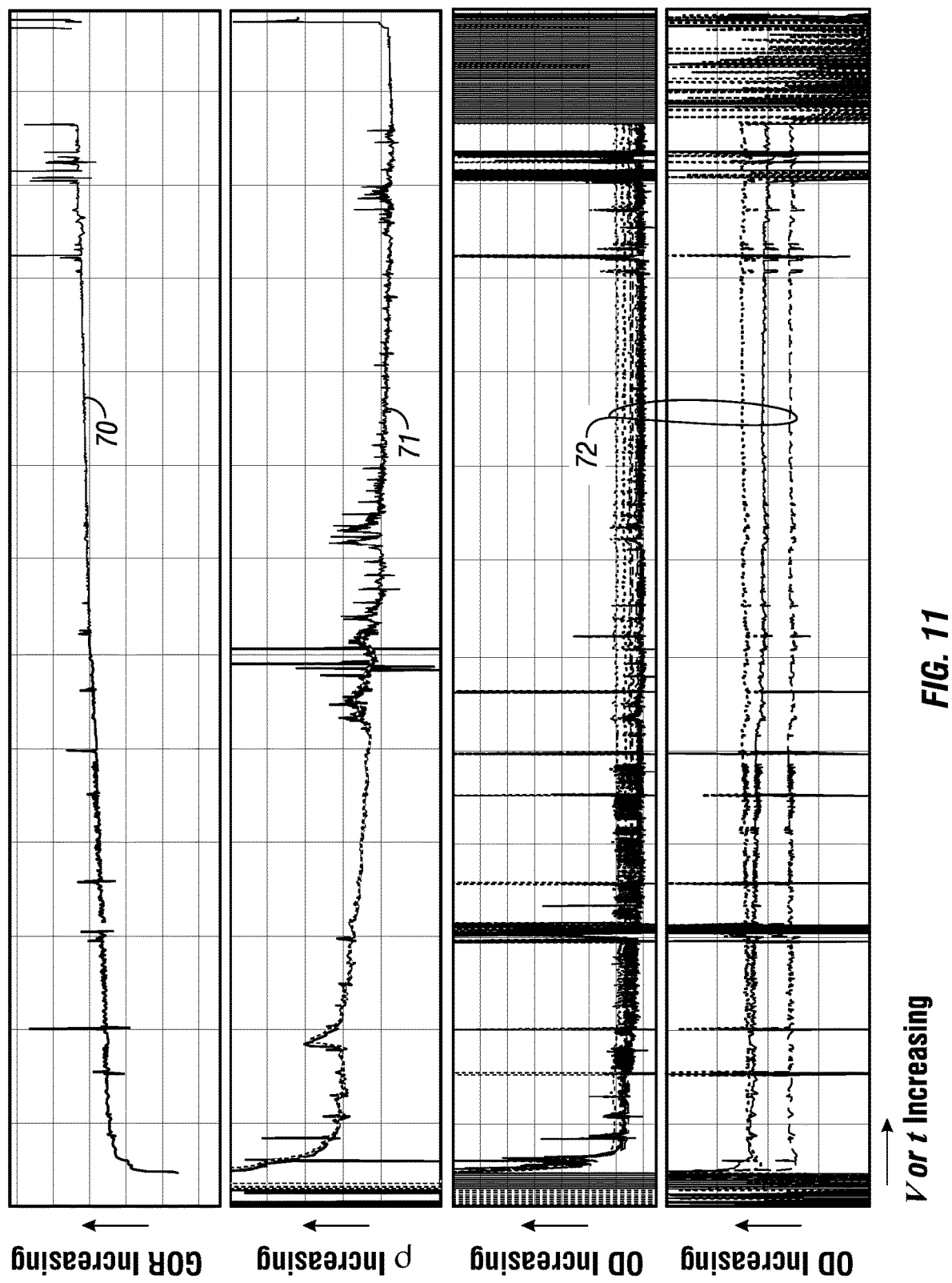
FIG. 11 includes four graphs each depicting one or more aspects of the present disclosure.

The cleanup data may include baseline-corrected $OD_i$, GOR, mass density $\rho$, pumped volume V (or pumping time t), and composition data, among other examples. An example of cleanup data for gas condensate is depicted in FIG. 11, in which apparent GOR (ft$^3$/bbl) is depicted as solid line 70, apparent density (g/cm$^3$) is depicted as solid line 71, and multi-channel OD (unit-less) is depicted as lines 72, 73, each as a function of pumped volume V (or pumping time t).

The cleanup data may be denoised (116) utilizing a filter or statistic method, such as the student-test method. It is noted that spikes may occur when pumpout starts and sample bottles are being filled.

The start of linear behavior may then be determined (120) by, for example, selecting an interval where the linear relationships hold in cross plots. Such interval may be different from the fitting interval described below. The start of linear behavior may be determined (120) by visual inspection of the cleanup data by a human operator. However, the start of linear behavior may also or instead be determined (120) by the processing means of the downhole sampling tool, the surface equipment, and/or other equipment. For example, the early time cleanup data may be compared to a linear fitting of the cleanup data, such that linearity may be determined (120) to have started when an R2 comparison of the cleanup data to the linear fitting is at least about 0.9. However, other methods for determining (120) the start of linear behavior are also within the scope of the present disclosure.

The molecular weight of gas $M_{gas}$ may then be determined (124). For example, the molecular weight of gas $M_{gas}$ may be determined (124) based on composition data input (104) with the cleanup data. However, other methods for determining (124) the molecular weight of gas $M_{gas}$ are also within the scope of the present disclosure.

The method (100) also includes determining (128) an estimated stock tank oil density $\rho_{STOStd}$ utilizing the cleanup data. For example, the stock tank oil density $\rho_{STOStd}$ may be determined by one or more of the methods described above with respect to Equations (4)-(6). The stock tank oil density $\rho_{STOStd}$ may also be determined (128) utilizing DFA data from a previously analyzed well if the same type of OBM was utilized.

The method (100) may also include estimating (132) $GOR_0$, the GOR of the native formation fluid. For example, $GOR_0$ may be estimated (132) utilizing one or more of Equations (12)-(19B) set forth above.

$B_o$, the formation volume factor of the native formation fluid, may then be determined (136) utilizing one or more of the determined (124) molecular weight of gas $M_{gas}$, the determined (128) stock tank oil density $\rho_{STOStd}$, and the estimated (132) GOR of the native formation fluid $GOR_0$. For example, $B_o$ may be determined (136) utilizing Equation (4), assuming the formation volume factor of OBM filtrate in the sampled fluid $B_{oobm}$ is equal to one (1). The shrinkage factor b may then be determined (140), such as via utilization of Equation (3) set forth above. The $f$ and g function may then be determined (144), such as may include utilizing Equation (12) set forth above. The power function fitting parameters described above, including the slope $\gamma$, may then be determined (148).

Thereafter, $OD_i$ and $\rho$ versus the $f$ function may be plotted to determine (152) their linear relationships. However, OD may not be shown in the crossplot vs. the $f$ function or in the OD-based contamination plot if there is insufficient contrast, because both filtrate and condensate are colorless. But if contrast exists (e.g., at an oil station), OD may be utilized.

Figure 12:
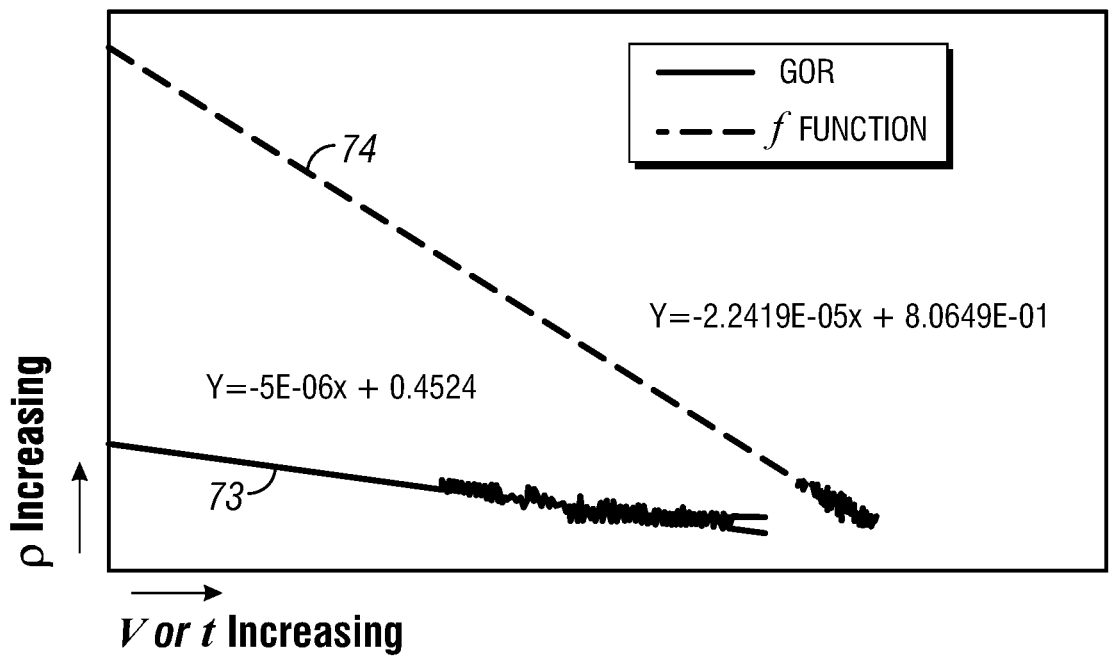
FIG. 12 is a graph depicting one or more aspects of the present disclosure.

FIG. 12 depicts an example plot for a gas condensate, including $\rho$ (g/cc) versus apparent GOR (solid line 73), and $\rho$ versus the $f$ function (dashed line 74), and the corresponding determined linear relationships. It is noted that $\rho$ (g/cc) versus apparent GOR is included to show the magnitude of the error if GOR is used instead of the $f$ function.

Determining (152) the linear relationships may utilize Equations (20) and (21) set forth below.

$$\rho = a + b_1 f \qquad (20)$$

$$OD_i = c_i + d_i f \qquad (21)$$

The linear relationships determined (152) utilizing Equations (20) and (21) may then be utilized to extrapolate (156) the $f$ function to zero to determine one or more properties of the OBM filtrate, such as $OD_{obmi}$ and $\rho_{obm}$, as set forth below in Equations (22) and (23).

$$\rho_{obm} = a \qquad (22)$$

$$OD_{obmi} = c_i \qquad (23)$$

However, in some environments, such as when oil GOR is very low, the density vs. OD plot and the $f$ function vs. OD plot may also be extrapolated to zero to obtain the filtrate properties.

It is also noted that if dual flowlines (guard and sample) are utilized for a focused sampling probe, the sample flowline may have substantially less OBM filtrate contamination relative to that of the guard flowline. Accordingly, the sample flowline may have a substantially larger GOR relative to that of the guard flowline. Therefore, more robust linear relationships and extrapolation in plots of density (or OD) versus the $f$ function may be obtained utilizing dual flowline information.

The linear relationships determined (152) utilizing Equations (20) and (21) may also be utilized to extrapolate (160) the g function to determine one or more properties of the native formation fluid (absent OBM filtrate contamination), such as $OD_{0i}$ and $\rho_0$, as set forth below in Equations (24) and (25).

$$\rho_0 = a + b_1 GOR_0 = \rho_{obm} + b_1 GOR_0 \quad (24)$$

$$OD_{0i} = c_i + d_i GOR_0 = OD_{obmi} + d_i GOR_0 \quad (25)$$

Similarly, with a density vs. OD plot, the oil density may be determined if the oil OD is known. Thus, if one of oil density, oil GOR, and oil OD is known, the other two can be determined.

In the gas condensate example depicted in FIG. 12, $\rho_{obm}$=0.8065 g/cc and $\rho_0$=0.3682 g/cc (the fitted $GOR_0$=18943 scf/bbl), as determined from the linear relationships shown therein. The density from the density fitting itself is 0.3721 g/cc. Both densities are close, differing by about one percent.

The method (100) may also include a comparison (164) of the properties (e.g., $OD_{0i}$, $\rho_0$, $OD_{obmi}$, and $\rho_{obm}$) of the pure native formation fluid and pure OBM filtrate extrapolated from the linear relationship with those from a power function fitting that utilizes the determined (148) fitting parameters. If they are not sufficiently close (e.g., within about five or ten percent of each other), the root cause of the discrepancy may be investigated to determine (166) which endpoints are more reliable, those of the interpolation or those of the power fitting. If they are sufficiently close, the end points may then be output (168). For example, such output (168) may include $OD_{0i}$, $\rho_0$, $GOR_0$, and $m_{0i}$ of the native formation fluid, and $OD_{obmi}$ and $\rho_{obm}$ of the OBM filtrate.

Figure 13:
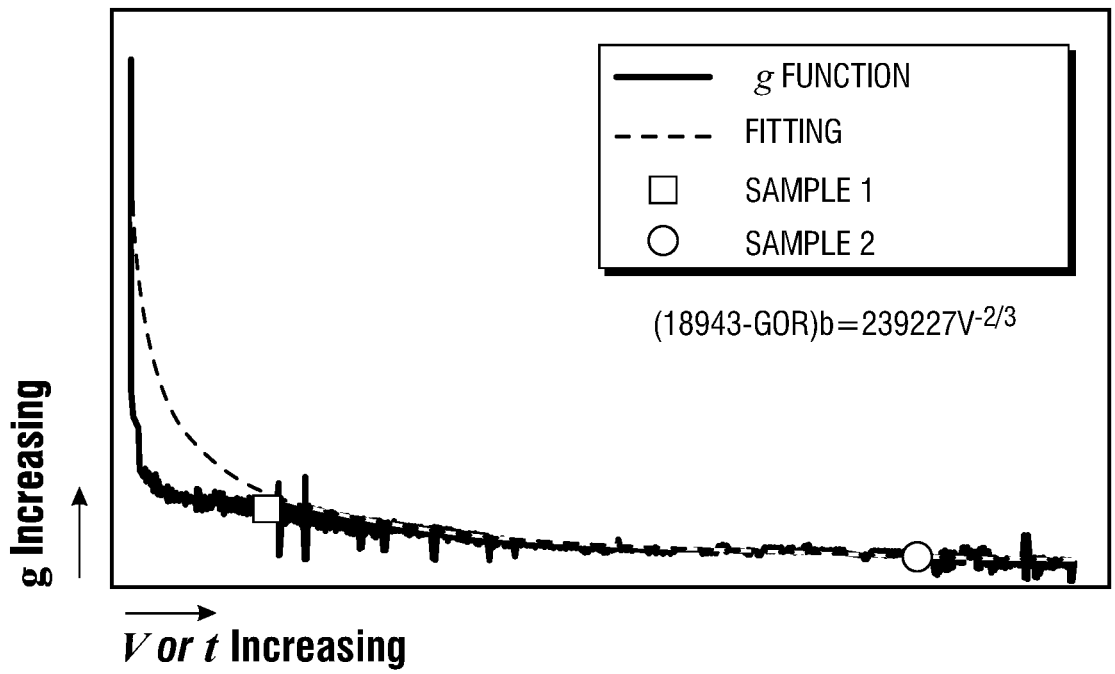
FIG. 13 is a graph depicting one or more aspects of the present disclosure.
Figure 14:
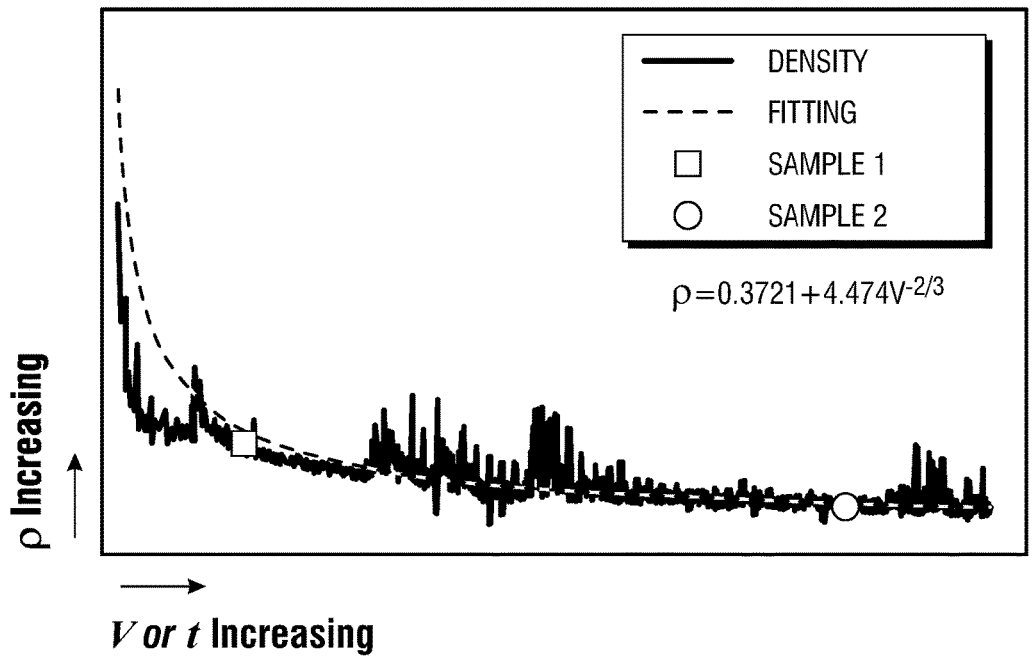
FIG. 14 is a graph depicting one or more aspects of the present disclosure.

Thereafter, the contamination level in volume fraction on the live formation fluid basis may be estimated (172) utilizing Equation (13). The example for gas condensate is depicted in FIGS. 13 and 14, depicting two example samples taken at different contamination levels. FIG. 13 shows the g function from the model and g function with measured data input. FIG. 14 shows modeled density and measured density. Both plots show the volumes at which samples are taken. The late time cleanup (e.g., when $v_{obm}$ is less than about three percent) follows a slope $\gamma$ of ⅔. Uncertainty analysis may then performed (176), including discriminating those with large uncertainty from multiple sensors.

The method (100) may also include averaging (180) the contamination levels from the g function and density fitting, and/or selecting (184) the contamination level with the least uncertainty. The averaged (180) and/or selected (184) contamination level in volume fraction on the live fluid basis may then be converted (188), such as to that in weight fraction on the live fluid basis via Equation (26) set forth below.

$$w_{obm} = \frac{v_{obm} \rho_{obm}}{\rho} = \frac{\rho_{obm}}{\rho} \frac{OD_{0i} - OD_i}{OD_{0i} - OD_{obmi}} = \frac{\rho_{obm}}{\rho} \frac{\rho_0 - \rho}{\rho_0 - \rho_{obm}} = \frac{\rho_{obm}}{\rho} \frac{(GOR_0 - GOR)b}{GOR_0} \quad (26)$$

The conversion (188) may also include converting to contamination level in volume fraction on the STO basis, such as via Equation (27) set forth below.

$$v_{obmSTO} = \frac{OD_{0i} - OD_i}{(OD_{0i} - OD_{obmi})b} = \frac{\rho_0 - \rho}{(\rho_0 - \rho_{obm})b} = \frac{GOR_0 - GOR}{GOR_0} \quad (27)$$

The conversion (188) may also include converting to contamination level in weight fraction on the STO basis, such as via Equation (28) set forth below.

$$w_{obmSTO} = \frac{\rho_{obmStd}}{\rho_{STOStd}} \frac{OD_{0i} - OD_i}{(OD_{0i} - OD_{obmi})b} = \quad (28)$$

$$\frac{\rho_{obmStd}}{\rho_{STOStd}} \frac{\rho_0 - \rho}{(\rho_0 - \rho_{obm})b} = \frac{\rho_{obmStd}}{\rho_{STOStd}} \frac{GOR_0 - GOR}{GOR_0}$$

The method (100) may also include determining (192) the uncontaminated formation fluid compositions, such as by assuming that OBM filtrate is heavier than C6, thus resulting in Equations (29) and (30) set forth below.

$$m_{0i} = \frac{m_i}{1 - w_{obm}}, i = C_1, C_2, C_3, C_4, C_5, CO_2 \quad (29)$$

$$m_{0C6+} = \frac{m_{C6+} - w_{obm}}{1 - w_{obm}} \quad (30)$$

where m is the composition in weight fraction.

The power function fitting of composition versus pumpout volume (or time) may also be applied to obtain the composition of uncontaminated fluid by extrapolating pumpout volume or time to infinity. This process may also be applied to other fluid properties, such as compressibility, formation volume factor, saturation pressure, and viscosity.

Because OBM contamination level and OBM filtrate properties are known, the mixing rules may be employed to compute properties of the pure virgin hydrocarbon fluid as well. For example, if density contrast is small, it may be difficult to obtain good fitting for density. Therefore, the density-mixing rule may be utilized to calculate density of the pure virgin hydrocarbon fluid.

The method (100) may also include converting (196) density and viscosity from flowline to formation conditions. That is, flowline conditions may be very different from formation conditions, such as if sensors are positioned downstream of the pumpout module where pressure is substantially greater than formation pressure. There are at least two ways to do this conversion (196).

First, an EoS (or/and viscosity) model may be established based on $m_{i0}$, such that density ($\rho_0$) or/and viscosity may be matched at flowline conditions, and density ($\rho_0$) or/and viscosity may be predicted at formation conditions. Second, based on the density versus pressure relation during sampling, one can obtain compressibility versus pressure, such as set forth below in Equation (31).

$$c = \frac{1}{\rho} \frac{\partial \rho}{\partial P} = \frac{\partial \ln \rho}{\partial P} \quad (31)$$

where c is compressibility, which is a function of pressure. This leads to Equation (32) set forth below.

$$\ln \rho_0 |_{formation} = \ln \rho_0 |_{flowline} + \int_{P\_flowline}^{P\_formation} c(P) dP \quad (32)$$

The method (100) described above, and/or related methods within the scope of the present disclosure, may include a power law extrapolation on the $f$ function. For example, this may be substantially similar to the extrapolation of the g function as described above, but perhaps shifted by a constant value (e.g., $GOR_0$). This may not add information over the g function extrapolation—such as in implementations in which the $f$ function or the g function would be selected with similar results—but may be a matter of preference based on available data, preliminary results, and/or other factors.

Figure 15:
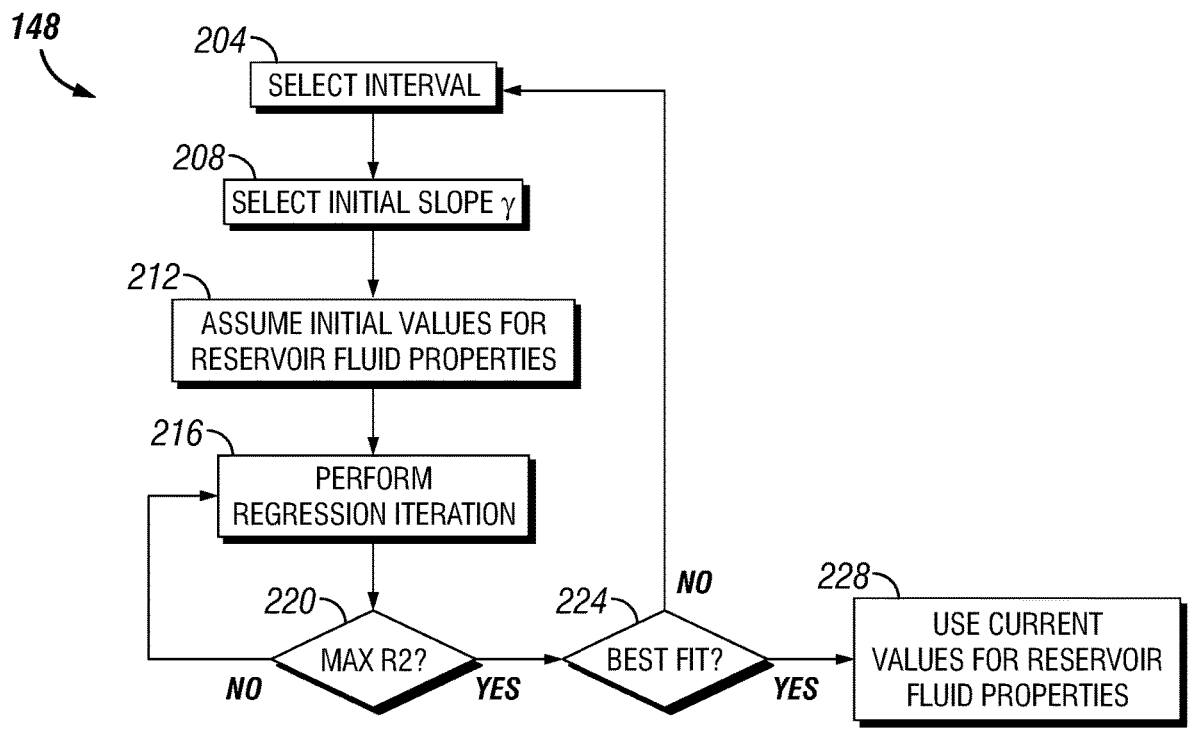
FIG. 15 is a flow-chart diagram of at least a portion of a method according to one or more aspects of the present disclosure.

FIG. 15 is a flow-chart diagram of an example of a method for determining (148) the fitting parameters described above with respect to FIG. 10. The method (148) may include selecting (204) start and end points of an interval to be utilized for power function fitting. Such selection (204) may be based on a flow regime identification method, among other examples.

The slope γ to be utilized for the power function fitting may then be initially selected (208). For example, if an unfocused radial sampling probe is utilized, and if $v_{obm}$ is less than about ten percent, a value of ⅔ may be initially selected (208) for the slope γ. If an unfocused single sampling probe (such as the unfocused sampling probes 64-66 shown in FIG. 7) is utilized, a value of 5/12 may be initially selected (208) of the slope γ for early time cleanup, and a value of ⅔ may be initially selected (208) for the slope γ for late time cleanup (such as when $v_{obm}$ is less than about three percent. For focused sampling probes, whether radial or otherwise, when the sample line reaches low contamination, there is an approximate linear relation between $v_{obm}$ and V (or t) in the log-log plot. However, the guard line may still have very high contamination. Thus, the sample line cleanup data may be utilized for the power function fitting, and the slope γ may be treated as an adjustable parameter that is much larger than one (e.g., γ>>⅔). Initial values of the reservoir fluid properties may then be assumed (212), such as $OD_{0i}$, $\rho_0$, $GOR_0$, and γ if γ is not fixed.

Figure 16:
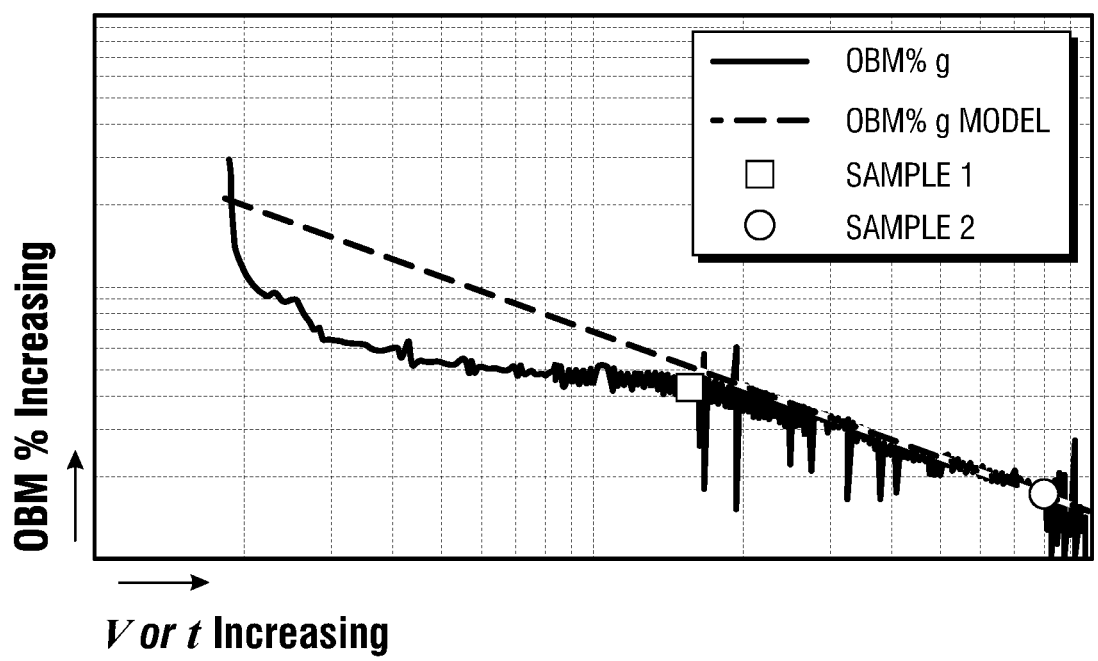
FIG. 16 is a graph depicting one or more aspects of the present disclosure.
Figure 17:
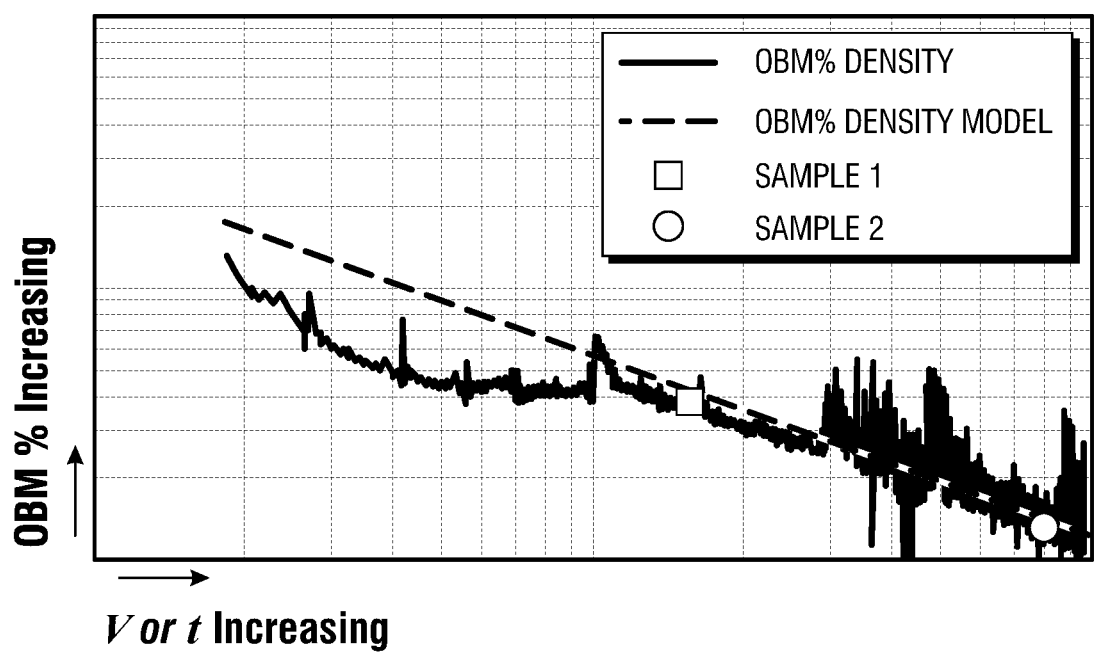
FIG. 17 is a graph depicting one or more aspects of the present disclosure.

An iteration of linear regression may then be performed (216), such as by utilizing Equations (17)-(19B). After each iteration of the linear regression is performed (216), the correlation coefficients R2 may be assessed (220) to determine if a best (maximum) correlation has been obtained. If they are not optimized, $OD_{0i}$, $\rho_0$, $GOR_0$, and γ (if γ is adjustable) may be updated. Example results for gas condensate are depicted in FIGS. 16 and 17. It is noted, however, that this optimization may also be performed via non-linear regression methods.

If it is determined (220) that the initial values for the reservoir fluid properties are optimized, a check of whether the best fitting is achieved may then be performed (224) by comparing endpoints of the pure reservoir fluid from different intervals. If it is determined (224) that best fitting has not been achieved, a different fitting interval may be selected (204), and the regression or other optimization may be repeated. If it is determined (224) that best fitting has been achieved, the current values for the reservoir fluid properties are utilized (228).

The objective of this plot is to visualize when the measured data (manipulated as per Equations (17), (18), and/or (19)) forms a straight line with slope γ so that the power law can be fit on that section of data that exhibits constant power law behavior, such as to avoid fitting a constant power law model on a varying power law dataset. When the start-fit is changed, the $OD_{0i}$, $\rho_0$, $GOR_0$, and γ (if γ is adjustable) also change, hence the iterative process described above.

One or more aspects of the method (100) and/or other aspects described above may find application in various DFA settings. For example, it can be assumed that a fluid is in a single-phase at downhole conditions. The phase may be liquid ("oil") or gas ("gas condensate"). The fluid may be flashed from downhole conditions to standard conditions (e.g., 14.7 psia and 60 degrees F.), resulting in flashed liquid ("stock-tank oil" or STO) and flashed gas. That is, the downhole ("live") fluid may have a volume V, a density ρ (known as apparent density), and a mass g, and may comprise OBM having a volume $v_{obm}$. The flashed gas may have a volume $V_g$, a molecular weight $MW_g$, a mass $m_g$, a number of moles $N_g$, and a mole ratio $n_g$ equal to $N_g/(N_g+N_{STO})$. The STO portion of the flashed liquid may have a volume $V_{STO}$, a density $\rho_{STO}$, a molecular weight $MW_{STO}$, a mass $M_{STO}$, and a number of moles $N_{STO}$, and the OBM portion of the flashed liquid may have a volume $V_{obmSTO}$. As with the description above, the subscripts 0 and obm in the following description designate properties of the pure formation fluid and the pure OBM filtrate, respectively.

According to the definition of the single-stage flash FVF described above, the FVF of the native formation fluid ($B_o$) may be determined as set forth below in Equation (33).

$$B_o = \frac{V}{V_{STO}} = \left(1 + \frac{GOR}{23.69} \frac{MW_g}{\rho_{STO}}\right)\frac{\rho_{STO}}{\rho} = \frac{\rho_{STO}}{\rho} + \frac{GOR}{23.69} \frac{MW_g}{\rho} \quad (33)$$

Equation (33) is similar to Equation (4) set forth above.

STO-based OBM filtrate contamination in volume fraction ($v_{obmSTO}$) may also be derived in terms of the GOR definition as set forth below in Equation (34).

$$v_{obmSTO} = \frac{V_{obmSTO}}{V_{STO}} = \frac{GOR_0 - GOR}{GOR_0} \quad (34)$$

Equation (34) is similar to Equation (5) set forth above.

Applying the density mixing rule (e.g., Equation (13) set forth above), and assuming that mixing the formation fluid with the OBM filtrate is ideal (e.g., that no excess volume is generated during mixing), the apparent density ρ may be expressed as set forth below in Equation (35).

$$\rho = v_{obm}\rho_{obm} + (1 - v_{obm})\rho_0 \quad (35)$$

Rearranging Equation (35) may yield the live-fluid-based OBM filtrate contamination in volume fraction $v_{obm}$, as set forth below in Equation (36).

$$v_{obm} = \frac{V_{obm}}{V} = \frac{\rho_0 - \rho}{\rho_0 - \rho_{obm}} \quad (36)$$

Equation (36) is similar to Equation (11) set forth above.

Based on one unit volume of the OBM-filtrate-contaminated fluid, $v_{obm}$ can be converted to STO-based OBM filtrate contamination in volume fraction ($v_{obmSTO}$) by formation volume factors. Because $V_{obmSTO} = V_{obm}/B_{oobm}$ (where $B_{oobm} = V_{obm}/V_{obmSTO} = \rho_{obmSTO}/\rho_{obm}$) and $V_{STO} = V/B_o$, converting Equation (36) and substituting it into Equation (34) results in Equation (37) set forth below.

$$v_{obmSTO} = \frac{V_{obm}B_o}{B_{oobm}} = \frac{\rho_0 - \rho}{\rho_0 - \rho_{obm}}\frac{B_o}{B_{oobm}} = \frac{GOR_0 - GOR}{GOR_0}, b = \frac{B_{oobm}}{B_o} \quad (37)$$

where b ($=B_{oobm}/B_o$) is the shrinkage factor.

The density mixing rule can also be directly applied to STO, resulting in Equation (38) set forth below.

$$\rho_{STO} = v_{obmSTO}\rho_{obmSTO} + (1-v_{obmSTO})\rho_{0STO} \quad (38)$$

Rearranging Equation (38) and substituting it into Equation (34) results in Equation (39) set forth below.

$$v_{obmSTO} = \frac{\rho_{0STO} - \rho_{STO}}{\rho_{0STO} - \rho_{obmSTO}} = \frac{(GOR_0 - GOR)}{GOR_0} \quad (39)$$

where $\rho_{0STO}$ and $\rho_{obmSTO}$ are respectively the STO density of the formation fluid and OBM filtrate, at standard conditions.

Rearranging Equation (33) may then result in Equation (40) set forth below.

$$B_o\rho - \rho_{STO} = \frac{GOR \cdot MW_g}{23.69} \quad (40)$$

Rearranging Equation (37) may then result in Equation (41) set forth below.

$$B_o\rho = \rho_0 B_o - \frac{(GOR_0 - GOR)(\rho_0 - \rho_{obm})B_{oobm}}{GOR_0} \quad (41)$$

Rearranging Equation (39) may then result in Equation (42) set forth below.

$$\rho_{STO} = \rho_{0STO} - \frac{(GOR_0 - GOR)(\rho_{0STO} - \rho_{obmSTO})}{GOR_0} \quad (42)$$

Operating both sides of Equations (40)-(42) by adding Equations (40) and (42) and subtracting Equation (41) may then result in Equation (43) set forth below.

$$B_o\rho - \rho_{STO} + \rho_{STO} - B_o\rho = \quad (43)$$
$$\frac{GOR \cdot MW_g}{23.69} + \rho_{0STO} - \frac{(GOR_0 - GOR)(\rho_{0STO} - \rho_{obmSTO})}{GOR_0} -$$
$$\rho_0 B_o + \frac{(GOR_0 - GOR)(\rho_0 - \rho_{obm})B_{oobm}}{GOR_0}$$

The left-hand side of Equation (43) is equal to zero, resulting in Equation (44) set forth below.

$$0 = \frac{GOR \cdot MW_g}{23.69} + \rho_{0STO} - \frac{(GOR_0 - GOR)(\rho_{0STO} - \rho_{obmSTO})}{GOR_0} - \quad (44)$$
$$\rho_0 B_o + \frac{(GOR_0 - GOR)(\rho_0 - \rho_{obm})B_{oobm}}{GOR_0}$$

Rearranging Equation (44) may then result in Equation (45) set forth below.

$$\rho_0 B_o = \frac{GOR \cdot MW_g}{23.69} + \rho_{0STO} - (\rho_{0STO} - \rho_{obmSTO}) + \quad (45)$$
$$\frac{GOR(\rho_{0STO} - \rho_{obmSTO})}{GOR_0} + (\rho_0 - \rho_{obm})B_{oobm} -$$
$$\frac{GOR(\rho_0 - \rho_{obm})B_{oobm}}{GOR_0} = \left[\frac{MW_g}{23.69} + \frac{(\rho_{0STO} - \rho_{obmSTO})}{GOR_0} - \right.$$
$$\left.\frac{(\rho_0 - \rho_{obm})_{oobm}}{GOR_0}\right]GOR + \rho_{obmSTO} + (\rho_0 - \rho_{obm})B_{oobm} =$$
$$\left[\frac{MW_g}{23.69} + \frac{(\rho_{0STO} - \rho_{obmSTO})}{GOR_0} - \frac{(\rho_0 B_{oobm} - \rho_{obmSTO})}{GOR_0}\right]GOR +$$
$$\rho_{obmStd} + (\rho_0 B_{oobm} - \rho_{obmSTO})$$

Obtaining Equation (45) included using Equation (46) set forth below, based on the assumption that OBM is not present in the gas phase.

$$\rho_{obmSTO} = B_{oobm}\rho_{obm} \quad (46)$$

Rearranging Equation (45) may then result in Equation (47) set forth below.

$$\rho_0 B_o = \left[\frac{MW_g}{23.69} + \frac{(\rho_{0STO} - \rho_0 B_{oobm})}{GOR_0}\right]GOR + \rho_0 B_{oobm} \quad (47)$$

Therefore, the FVF may be expressed as set forth below in Equation (48).

$$B_o = \left[\frac{MW_g}{23.69\rho_0} + \frac{(\rho_{0STO} - \rho_0 B_{oobm})}{\rho_0 GOR_0}\right]GOR + B_{oobm} = \quad (48)$$
$$\frac{B_{o0} - B_{oobm}}{GOR_0}GOR + B_{oobm}$$

The reciprocal of the shrinkage factor b may then be written as set forth below in Equation (49).

$$\frac{1}{b} = \frac{B_o}{B_{oobm}} = \frac{\frac{B_{o0}}{B_{oobm}} - 1}{GOR_0}GOR + 1 = \frac{\frac{1}{b_0} - 1}{GOR_0}GOR + 1 \quad (49)$$

At a specified DFA station, the OBM filtrate properties (e.g., $B_{oobm}$) and the formation fluid properties (e.g., $GOR_0$, $\rho_0$, and $\rho_{0STO}$) are fixed during the cleanup phase, because the OBM filtrate is assumed to not be present in the gas (vapor) phase, such that $MW_g$ remains constant. Therefore, the coefficient of GOR on the right-hand side of Equation (49) is constant. Thus, the reciprocal of the shrinkage factor is linearly associated with GOR, and also passes through the point of 1 (interception=1) at GOR=0, where it is the OBM filtrate ($B_o = B_{oobm}$ and $1/b = 1$). Accordingly, Equation (49) may be rewritten as set forth below in Equation (50).

$$\frac{1}{b} = \frac{B_o}{B_{oobm}} = k_1 GOR + 1 \quad (50)$$

The coefficient $k_1$ (slope) is given by Equation (51) set forth below.

$$k_1 = \left[\frac{MW_g}{23.69\rho_0 B_{oobm}} + \frac{(\rho_{0STO} - \rho_0 B_{oobm})}{\rho_0 GOR_0 B_{oobm}}\right] = \frac{\frac{B_{o0}}{B_{oobm}} - 1}{GOR_0} = \frac{\frac{1}{b_0} - 1}{GOR_0} \quad (51)$$

where the interception=1 in the plot of 1/b versus GOR.

Figure 18:
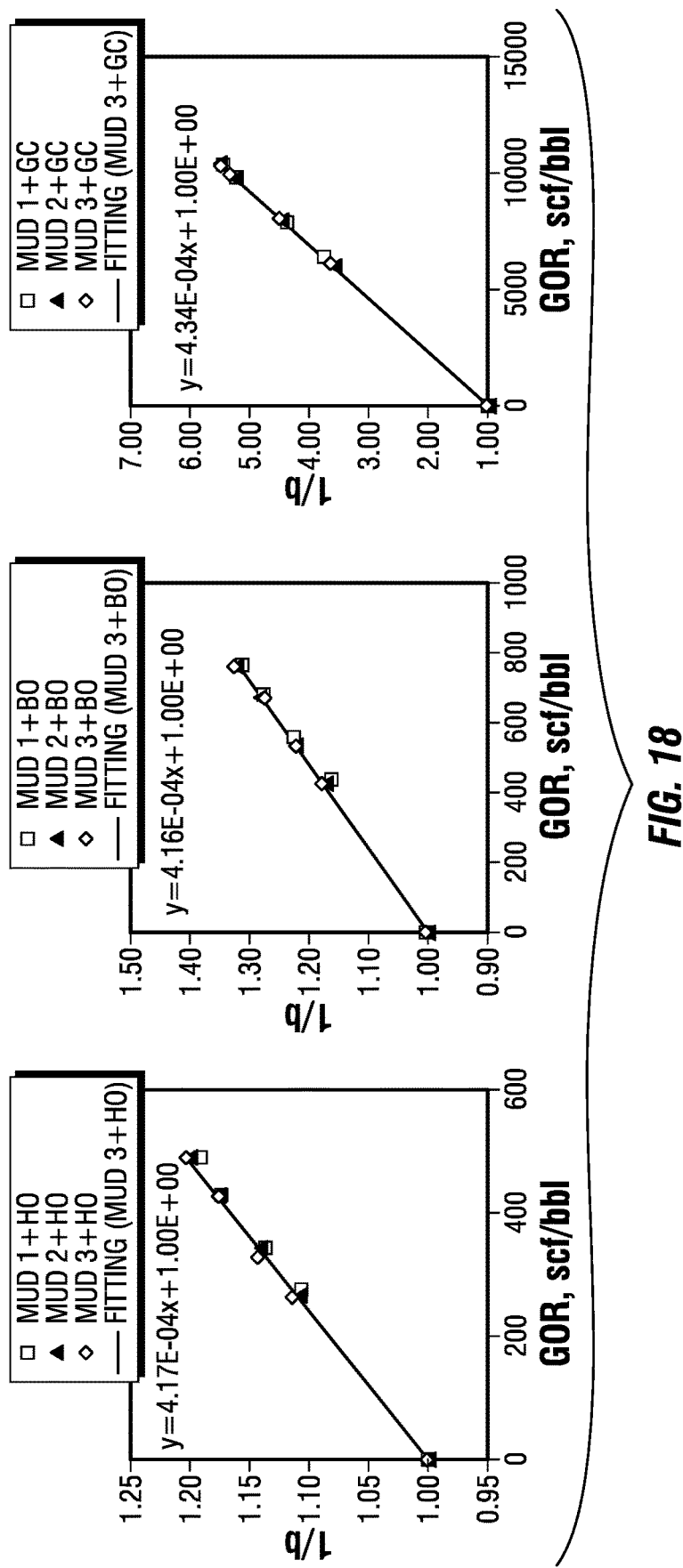
FIG. 18 includes three graphs each depicting one or more aspects of the present disclosure.

To confirm this linear relation, experiments were conducted by mixing a heavy oil (HO), a black oil (BO), and a gas condensate (GC) with three types of OBM filtrate (named as Muds 1, 2, and 3) at different OBM contamination levels. The results are shown in FIG. 18, in which it can be seen that 1/b versus GOR is linear over an entire OBM contamination range, from the pure OBM filtrate to the native formation fluid.

Rearranging Equation (42) may then result in Equations (52) and (53) set forth below.

$$\rho_{STO} = \rho_{obmSTO} + \frac{(\rho_{0STO} - \rho_{obmSTO})GOR}{GOR_0} = \rho_{obmSTO} + k_2 GOR \quad (52)$$

$$k_2 = \frac{(\rho_{0STO} - \rho_{obmSTO})}{GOR_0} \quad (53)$$

The STO density is linearly related to GOR during cleanup. Thus, once STO density is known with respect to GOR and $k_2$, the STO density may be populated using GOR. If two points are known, the linear relationship may be determined.

Figure 19:
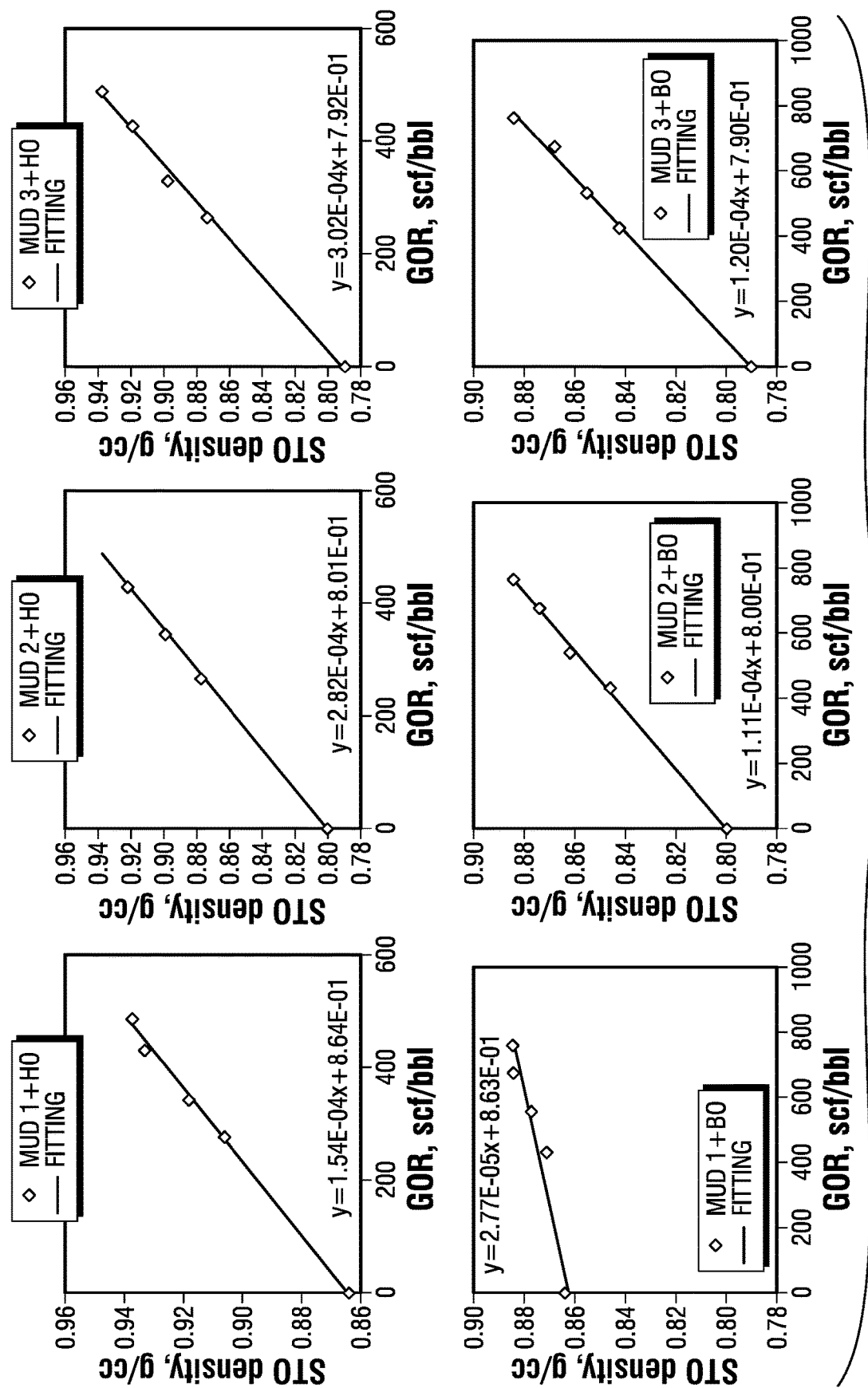
FIG. 19 includes six graphs each depicting one or more aspects of the present disclosure.

FIG. 19 depicts laboratory data for the heavy oil (HO) and black oil (BO) mixed with three types of OBM filtrates. It can be seen in FIG. 19 that the STO density is linearly related with GOR over the entire OBM contamination range, from the pure OBM filtrate to the native formation fluid.

In the following description, the superscript * represents an initial estimate or an intermediate determination of the corresponding value, and the corresponding parameters without the superscript * represent a "final" determined output, in a sense that is at least analogous to an iterative process. For example, $\rho^*_{STO}$ may be an initial estimate or intermediate determination of the density of STO, whereas $\rho_{STO}$ may be the ultimately determined density of STO.

Figure 20:
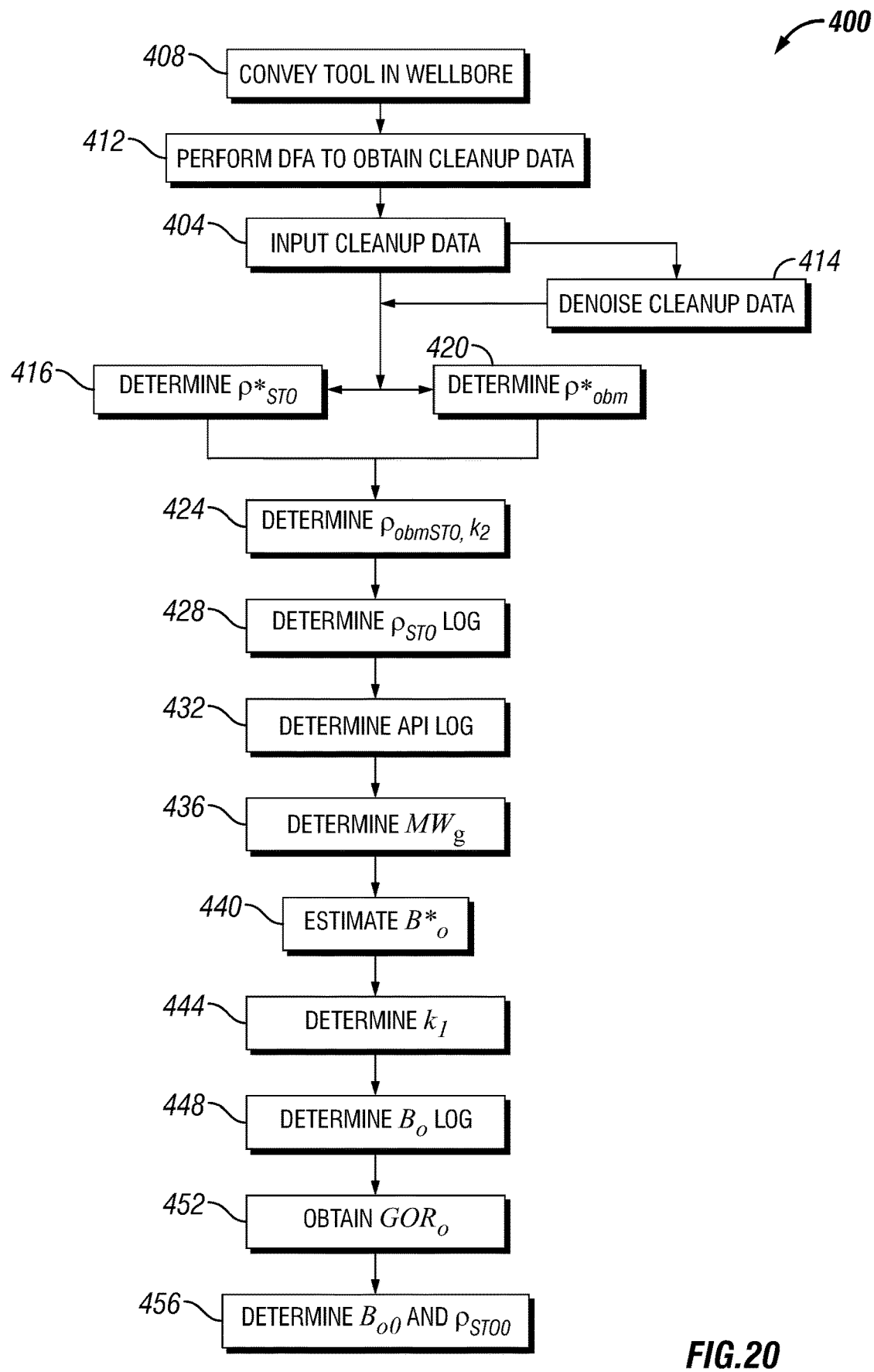
FIG. 20 is a flow-chart diagram of at least a portion of a method according to one or more aspects of the present disclosure.

The linear relations can be applied to obtain logs of FVF and API gravity (STO density) and those of the native formation fluids. For example, FIG. 20 is a flow-chart diagram of at least a portion of a method (400) representing an example workflow for such application. The method (400) includes inputting (404) cleanup data, such as may include DFA composition data (e.g., weight fractions of C1, C2, C3-C5, C6+, and CO2, although other composition schemes are also within the scope of the present disclosure), density ρ, and GOR, each with respect to pumped volume V or pumping time t. The method (400) may also include conveying (408) the downhole sampling tool in a wellbore to a subterranean formation penetrated by the wellbore, and operating (412) the downhole sampling tool and/or surface equipment in communication with the downhole sampling tool to obtain the cleanup data. The downhole sampling tool and/or surface equipment may then perform the cleanup data input (404) and/or the following actions, whether autonomously or in conjunction with a human operator's actions.

The cleanup data may then be denoised (414) utilizing a filter or statistic method, such as the student-test method. The density $\rho^*_{STO}$ may then be determined (416) from the input (904) or denoised (914) data, such as via artificial neural network (ANN) processing (such as may be a by-product of the GOR algorithm). An initial estimate of $\rho^*_{obm}$, may also be determined (420), such as from prior information. The determined (416) density $\rho^*_{STO}$ as a function of GOR may then be fit to determine (424) $\rho_{obmSTO}$ and $k_2$ in Equation (52) set forth above. The density $\rho_{STO}$ may then be determined (428) using Equation (52) based on GOR, thus obtaining the $\rho_{STO}$ log. The API gravity may then be determined (432) to provide an API gravity log, such as by utilizing Equation (54) set forth below.

$$API = \frac{141.5}{\rho_{STO}} - 131.5 \quad (54)$$

The composition and/or ANN processing may then be utilized to determine (436) $MW_g$. An initial $B^*_o$ may then be estimated (440) from $MW_g$ and $\rho_{STO}$, such as by utilizing Equation (33) set forth above. $B_o$ from the estimated $B^*_o$ data may then be fit, such as by using Equation (50) set forth above, to determine (444) $k_1$. $B_o$ based on GOR may then be determined (448), such as by utilizing Equation (50) set forth above, thus providing the $B_o$ log. The above-described OCM process may then be utilized to obtain (452) $GOR_0$, such as by performing a portion of the method (100) shown in FIG. 10 $B_{oO}$ and $\rho_{STOo}$ may then be determined (456), such as by substituting $GOR_0$ into Equations (50) and (52) set forth above.

Figure 21:
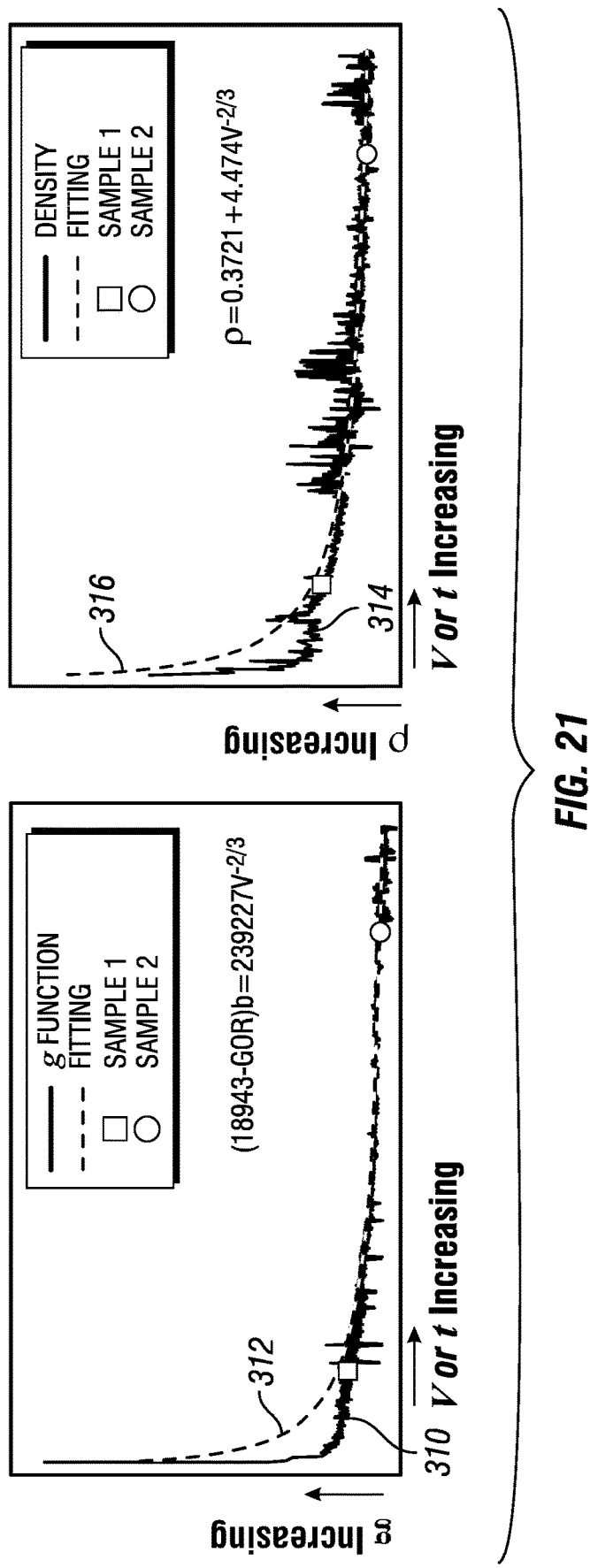
FIG. 21 includes two graphs each depicting one or more aspects of the present disclosure.
Figure 22:
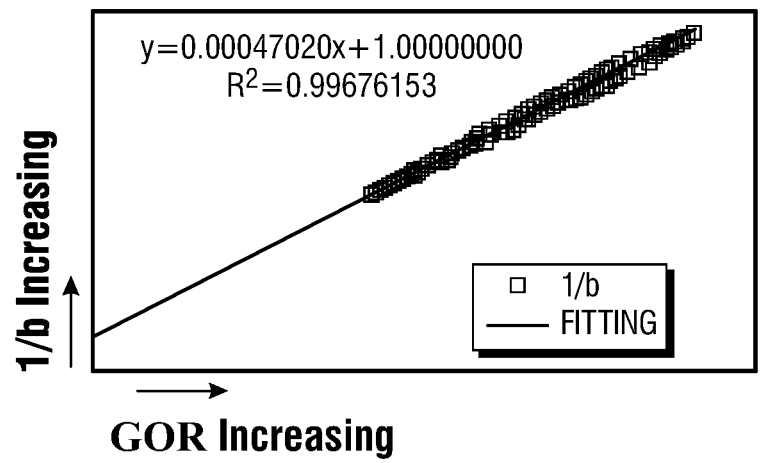
FIG. 22 is a graph depicting one or more aspects of the present disclosure.
Figure 23:
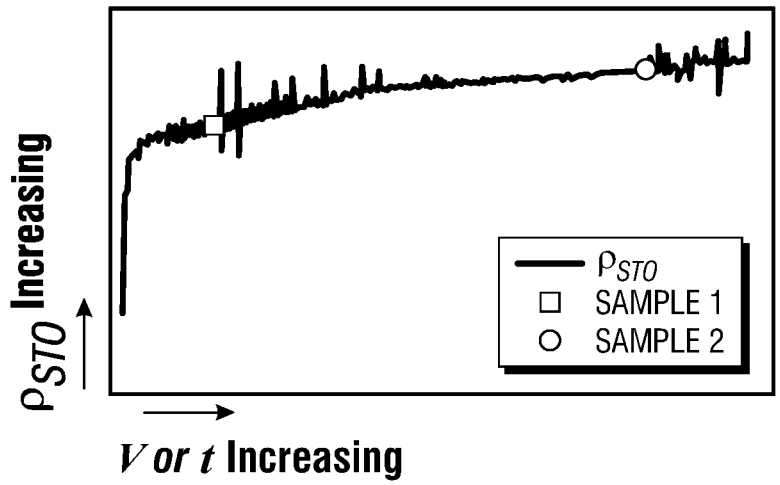
FIG. 23 is a graph depicting one or more aspects of the present disclosure.
Figure 24:
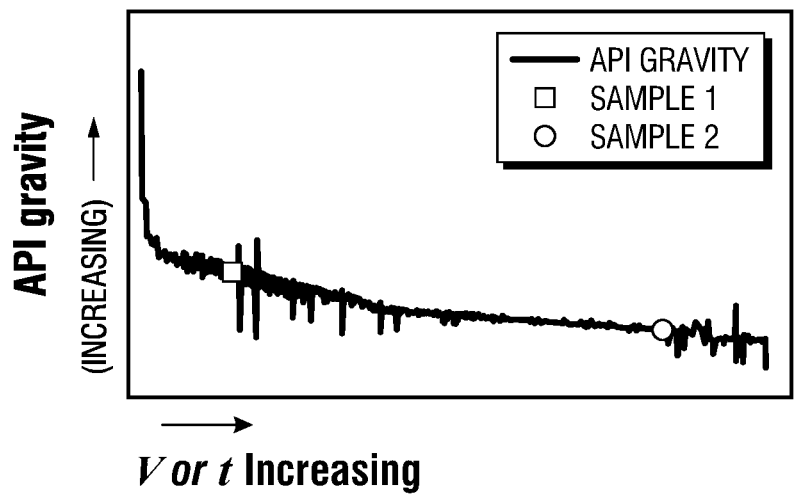
FIG. 24 is a graph depicting one or more aspects of the present disclosure.
Figure 25:
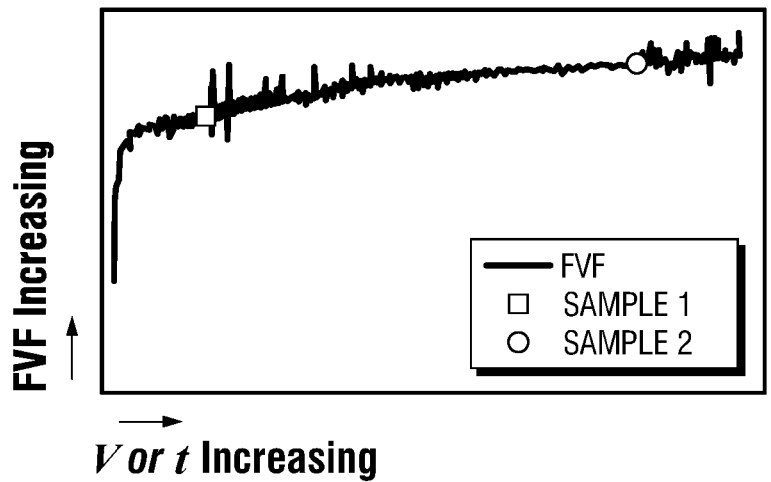
FIG. 25 is a graph depicting one or more aspects of the present disclosure.

An example for gas condensate is shown in FIG. 21, including example results for g function (line 310) and the associated fitting (line 312) and example results for density (line 314) and the associated fitting (line 316). In the example shown in FIG. 21, $GOR_0$=18,943 scf/bbl, and $\rho_0$=0.3721 g/cc. FIG. 22 shows the associated plot of 1/b versus GOR, demonstrating a substantially linear fitting, with an $R^2$ value close to 1. In the example associated with FIGS. 21 and 22, $k_1$=4.702×10$^{-4}$ bbl/scf. FIGS. 23-25 show the related logs of STO density, API gravity, and FVF, respectively.

Continuing with this example, because $GOR_0$=18,943 scf/bbl, the native formation fluid STO density may be determined as 0.8244 g/cc (see FIG. 23), the API gravity may be determined as 40.1° API (see FIG. 24), and the FVF may be determined as 9.9 (see FIG. 25). The related laboratory results were in substantial agreement at 0.8227 g/cc, 40.5° API, and 10.9, respectively.

Figure 26:
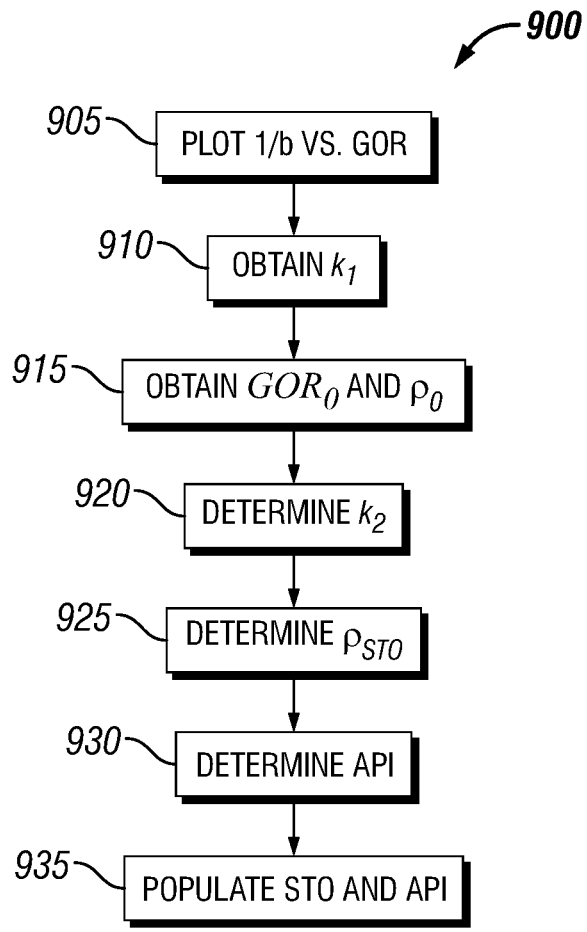
FIG. 26 is a flow-chart diagram of at least a portion of a method according to one or more aspects of the present disclosure.

FIG. 26 is a flow-chart diagram of at least a portion of a method (900) representing another example workflow according to one or more aspects of the present disclosure. The method (900) may include plotting (905) 1/b versus GOR and then obtaining (910) the linear relation with slope $k_1$. An OCM algorithm may then be utilized to obtain (915) $GOR_0$ and $\rho_0$ of the native formation fluid. Assuming $B_{oobm}$=1, Equation (51) may be utilized to obtain Equation (55) set forth below.

$$\rho_{0STO} = \rho_0 + \left(k_1 \rho_0 GOR_0 - \frac{MW_g GOR_0}{23.69}\right) \quad (55)$$

Equation (53) set forth above may then be utilized to determine (920) $k_2$, because $\rho_{obmSTO}$, $\rho_{0STO}$, and $GOR_0$ are known. Equation (52) may then be utilized to determine (925) $\rho_{STO}$, and Equation (54) may be utilized to determine (930) API gravity. The STO density and API gravity versus pumped volume and/or pumping time (from the STO density and API logs) may then be populated (935).

Figure 27:
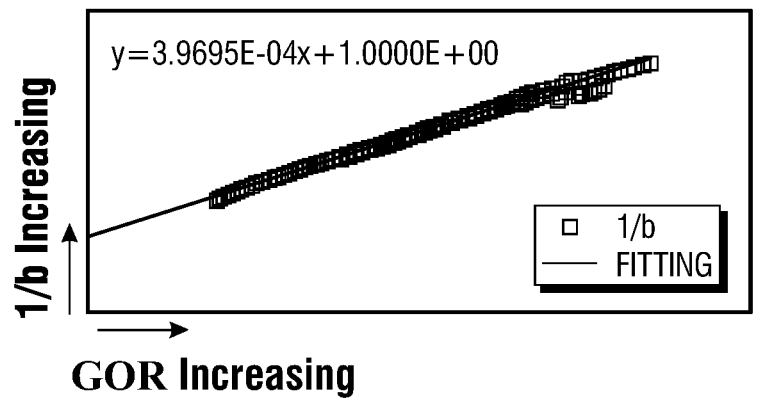
FIG. 27 is a graph depicting one or more aspects of the present disclosure.
Figure 28:
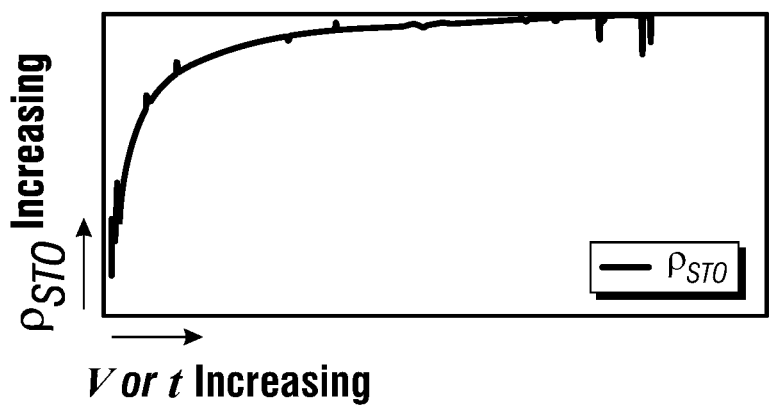
FIG. 28 is a graph depicting one or more aspects of the present disclosure.
Figure 29:
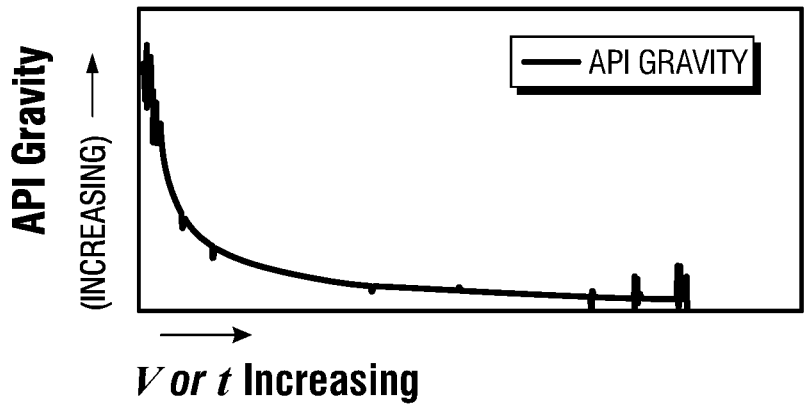
FIG. 29 is a graph depicting one or more aspects of the present disclosure.

An example for black oil is shown in the plot of 1/b versus GOR depicted in FIG. 27. The slope $k_1=3.9695\times 10^{-4}$ bbl/scf, $\rho_{obmSTO}=0.807$ g/cc, $\rho_0=0.754$ g/cc, and $GOR_0=1,189$ scf/bbl. Thus, the STO density of the native formation fluid is $\rho_{0STO}=0.9145$ g/cc. This also permits determining that $k_2=9.0442\times 10^{-5}$ bbl/scf. Therefore, the STO density and API gravity logs may be populated, as shown in FIGS. 28 and 29.

The linear relations determined as described above may also be applied to populate STO density and 1/b logs with GOR, time, and pumpout volume. Accordingly, one can obtain more reliable g function fitting and $f$ function extrapolation, thus yielding more reliable endpoints of the pure OBM filtrate and pure formation fluid, as well as more reliable OBM filtrate contamination.

Figure 30:
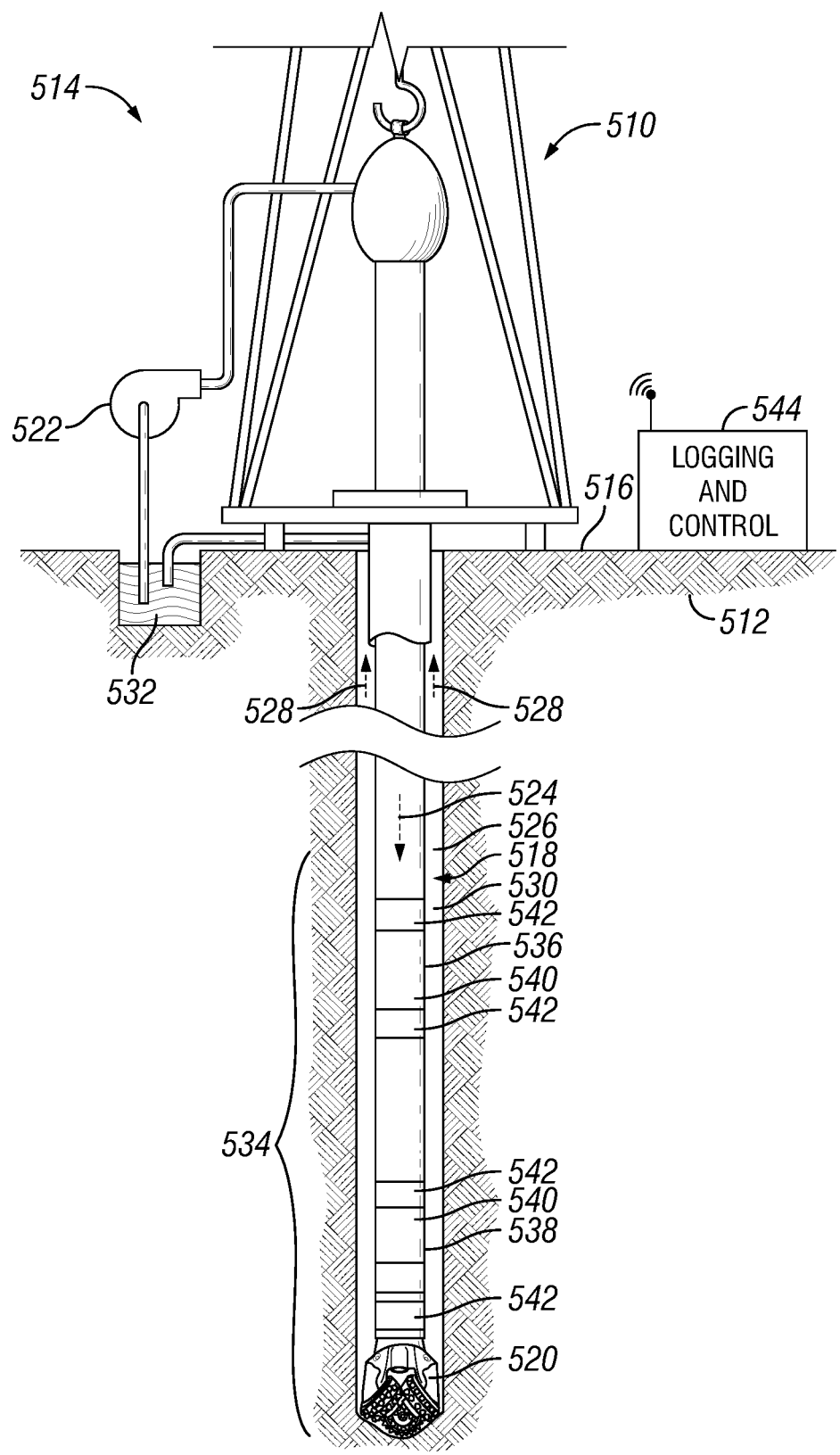
FIG. 30 is a schematic view of at least a portion of apparatus according to one or more aspects of the present disclosure.

FIG. 30 is a schematic view of at least a portion of a drilling system 510 operable to drill a wellbore 526 into one or more subsurface formations 512. One or more aspects described above may be performed by or in conjunction with one or more aspects of the drilling system 510 shown in FIG. 30.

A drilling rig 514 at the wellsite surface 516 is operable to rotate a drill string 518 that includes a drill bit 520 at its lower end. As the drill bit 520 is rotated, a pump 522 pumps OBM downward through the center of the drill string 518 in the direction of the arrow 524 to the drill bit 520. The OBM cools and lubricates the drill bit 520 and exits the drill string 518 through ports (not shown) in the drill bit 520. The OBM then carries drill cuttings away from the bottom of the wellbore 526 as it flows back to the wellsite surface 516 through an annulus 530 between the drill string 518 and the formation 512, as shown by the arrows 528. At the wellsite surface 516, the return OBM is filtered and conveyed back to a mud pit 532 for reuse.

While a drill string 518 is illustrated in FIG. 30, it will be understood that implementations described herein may be applicable or readily adaptable to work strings and wireline tools as well. Work strings may include a length of tubing (e.g., coiled tubing) lowered into the wellbore 526 for conveying well treatments or well servicing equipment. Wireline tools may include formation testing tools suspended from a multi-conductor cable as the cable is lowered into the wellbore 526 to measure formation properties at desired depths.

The location and environment of the drilling system 510 may vary depending on the formation 512 penetrated by the wellbore 526. Instead of being a surface operation, for example, the wellbore 526 may be formed under water of varying depths, such as on an ocean bottom surface. Certain components of the drilling system 510 may be specially adapted for underwater wells in such instances.

The lower end of the drill string 518 includes a bottom-hole assembly (BHA) 534, which includes the drill bit 520 and a plurality of drill collars 536, 538. The drill collars 536, 538 may include various instruments, such as sample-while-drilling (SWD) tools that include sensors, telemetry equipment, and so forth. For example, the drill collars 536, 538 may include logging-while-drilling (LWD) modules 540 and/or measurement-while drilling (MWD) modules 542 that may comprise one or more of the probes 64-66 and/or 68 shown in FIG. 7 for obtaining a sample of fluid from the formation 512. The LWD modules or tools 540 may include tools operable to measure formation parameters and/or fluid properties, such as resistivity, porosity, permeability, sonic velocity, OD, pressure, temperature, and/or others. The MWD modules or tools 542 may include tools operable to measure wellbore trajectory, borehole temperature, borehole pressure, and so forth. The LWD modules 540 may each be housed in one of the drill collars 536, 538, and may each contain one or more logging tools and/or fluid sampling devices. The LWD modules 540 include capabilities for measuring, processing, and/or storing information, as well as for communicating with the MWD modules 542 and/or with surface equipment such as, for example, a logging and control unit 544. That is, the SWD tools (e.g., LWD and MWD modules 540, 542) may be communicatively coupled to the logging and control unit 544 disposed at the wellsite surface 516. In other implementations, portions of the logging and control unit 544 may be integrated with downhole features.

The LWD modules 540 and/or the MWD modules 542 may include a downhole formation fluid sampling tool operable to selectively sample fluid from the formation 512. The drilling system 510 may be operable to determine, estimate, or otherwise obtain various properties associated with the sampled formation fluid. These properties may be determined within or communicated to the logging and control unit 544, such as for subsequent utilization as input to various control functions and/or data logs, including as described above for OCM purposes.

Figure 31:
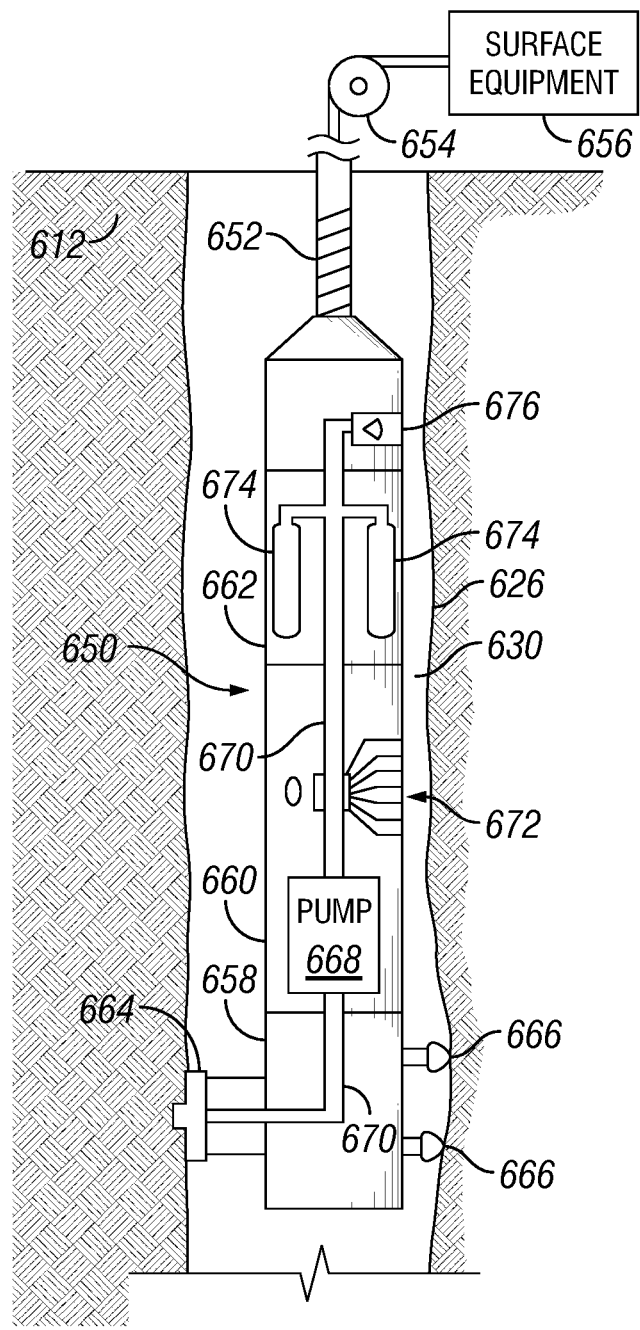
FIG. 31 is a schematic view of at least a portion of apparatus according to one or more aspects of the present disclosure.

FIG. 31 is a schematic diagram of an embodiment of downhole equipment (equipment configured for operation downhole) operable to sample fluid from a formation, such as the formation(s) 512 shown in FIG. 30. The downhole equipment includes an example embodiment of a downhole formation fluid sampling tool 650, hereinafter referred to as the downhole tool 650. The downhole tool 650 is conveyable within the wellbore 526 to the subsurface formation 512 and subsequently operable to sample formation fluid from the formation 512. In the illustrated embodiment, the downhole tool 650 is conveyed in the wellbore 526 via a wireline 652. The downhole tool 650 may be suspended in the wellbore 526 from a lower end of the wireline 652, which may be a multi-conductor cable spooled from a winch 654 at the surface. The wireline 652 may be electrically coupled to wellsite surface equipment 656, such as to communicate various control signals and logging information between the downhole tool 650 and the wellsite surface equipment 656. The wellsite surface equipment 656 shown in FIG. 31 and the logging and control unit 544 shown in FIG. 30, or functions thereof, may be integrated in a single system at the wellsite surface 516.

The downhole tool 650 includes a probe module 658, a pumpout module 660, and a sample module 662, one or more of which may comprise, be part of, be substantially similar to, or otherwise have similar functionality relative to one or more of the SWD tools, LWD modules 540, and/or MWD modules 542 shown in FIG. 30 and/or described above. However, other arrangements and/or modules may make up the downhole tool 650.

The probe module 658 may comprise a probe 664 operable to engage the formation 512 and communicate fluid samples from the formation 512 into the downhole tool 650. The probe 664 may be, comprise, or be substantially similar to one or more of the probes 64-66 and/or 68 shown in FIG. 7. The probe module 658 may also comprise one or more setting mechanisms 666. The setting mechanisms 666 may include pistons and/or other apparatus operable to improve sealing engagement and thus fluid communication between the formation 512 and the probe 664. The probe module 658 may also comprise one or more packer elements (not shown) that inflate or are otherwise operable to contact an inner wall of the wellbore 526, thereby isolating a section of the wellbore 526 for sampling. The probe module 658 may also comprise electronics, batteries, sensors, and/or hydraulic components used, for example, to operate the probe 664 and/or the corresponding setting mechanisms 666.

The pumpout module 660 may comprise a pump 668 operable to create a pressure differential that draws the formation fluid in through the probe 664 and pushes the fluid through a flowline 670 of the downhole tool 650. The pump 668 may comprise an electromechanical, hydraulic, and/or other type of pump operable to pump formation fluid from the probe module 658 to the sample module 662 and/or out of the downhole tool 650. The pump 668 may operate as a piston displacement unit (DU) driven by a ball screw coupled to a gearbox and an electric motor, although other types of pumps 668 are also within the scope of the present disclosure. Power may be supplied to the pump 668 via other components located in the pumpout module 660, or via a separate power generation module (not shown). During a sampling period, the pump 668 moves the formation fluid through the flowline 670 toward the sample module 662.

The pumpout module 660 may also include a spectrometer 672 operable to measure characteristics of the formation fluid as it flows through the flowline 670. The spectrometer 672 may be located downstream or upstream of the pump 668. The characteristics sensed by the spectrometer 672 may include OD of the formation fluid. Data collected via the spectrometer 672 may be utilized to control the downhole tool 650. For example, the downhole tool 650 may not operate in a sample collection mode until the formation fluid flowing through the flowline 670 exhibits characteristics of a clean formation fluid sample, as detected by or otherwise determined in conjunction with operation of the spectrometer 672. A clean formation fluid sample contains a relatively low level of contaminants (e.g., drilling mud filtrate) that are miscible with the formation fluid when extracted from the formation 512. Such contamination level may be determined according to one or more of the aspects described above, including with respect to the methods shown in FIGS. 10, 20, and/or 26.

The sample module 662 may comprise one or more sample bottles 674 for collecting samples of the formation fluid. Based on the OD and/or other characteristics of the formation fluid detected via sensors (e.g., the spectrometer 672) along the flowline 670, the downhole tool 650 may be operated in a sample collection mode or a continuous pumping (cleanup) mode. When operated in the sample collection mode, valves (not shown) disposed at or near entrances of the sample bottles 674 may be positioned to allow the formation fluid to flow into the sample bottles 674. The sample bottles 674 may be filled one at a time, and once a sample bottle 674 is filled, its corresponding valve may be moved to another position to seal the sample bottle 674. When the valves are closed, the downhole tool 650 may operate in a continuous pumping mode.

In the continuous pumping mode, the pump 668 moves the formation fluid into the downhole tool 650 through the probe 664, through the flowline 670, and then out of the downhole tool 650 through an exit port 676. The exit port 676 may be a check valve that releases the formation fluid into the annulus 530 of the wellbore 526. The downhole tool 650 may operate in the continuous pumping mode until the formation fluid flowing through the flowline 670 is determined to be clean enough for storing. That is, when the formation fluid is first obtained from the formation 512, OBM filtrate that has been forced into the formation 512 via the drilling operations may enter the downhole tool 650 along with the obtained formation fluid. After pumping the formation fluid for an amount of time, the formation fluid flowing through the downhole tool 650 will provide a cleaner fluid sample of the formation 512 than would otherwise be available when first drawing fluid in through the probe 664. For example, the formation fluid may be considered clean when the OD data from the spectrometer 672 is processed as described above and indicates that the formation fluid contains less than approximately 1%, 5%, or 10% OBM filtrate contamination (by volume), although other values are also within the scope of the present disclosure.

The characteristics of the formation fluid measured by the spectrometer 672 may be useful for performing a variety of evaluation and control functions, in addition to determining when the formation fluid flowing through the flowline 670 is clean enough for storing. For example, data may be collected from the spectrometer 672 and/or other sensors within the downhole tool, such as a density sensor, a viscosity sensor, a pressure sensor, a temperature sensor, and/or a saturation pressure sensor, among others. The collected data may be utilized to estimate a formation volume factor of the contaminated formation fluid, as well as density, optical density, GOR, compressibility, saturation pressure, viscosity, and/or mass fractions of compositional components of the contaminated formation fluid and/or contaminants therein (e.g., OBM filtrate), among others.

Figure 32:
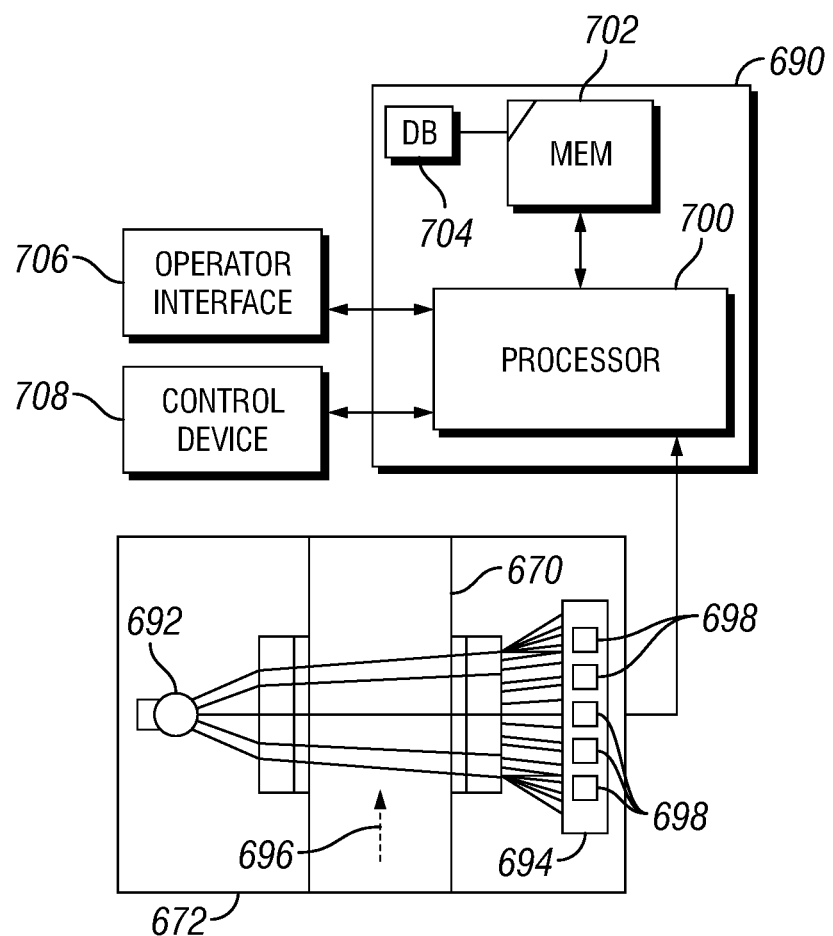
FIG. 32 is a schematic view of at least a portion of apparatus according to one or more aspects of the present disclosure.

FIG. 32 is a schematic diagram of the spectrometer 672 and a control/monitoring system 690 that may be utilized to estimate or determine one or more of such properties. The spectrometer 672 may comprise a light source 692 and a detector 694 disposed on opposite sides of the flowline 670 through which the formation fluid flows, as indicated by arrow 696. The spectrometer 672 may be part of the downhole tool 650, and may be located at various possible locations along the flowline 670 that directs the formation fluid through the downhole tool 650. Although a single light source 692 is depicted in the example shown in FIG. 32, the spectrometer 672 may include additional light sources 692. The detector 694 may sense the light that passes through the formation fluid in the flowline 670.

The detector 694 may include one or more detector elements 698 that may each be operable to measure the amount of light transmitted at a certain wavelength. For example, the detector elements 698 may detect the light transmitted from the visible to near-infrared within a range of 1, 5, 10, 20, or more different wavelengths ranging between about 400 nm and about 2200 nm. However, other numbers of wavelengths (corresponding to the number of detector elements) and other ranges of wavelengths are also within the scope of the present disclosure. For example, optical characteristics of the formation fluid may be detected at a range of wavelengths, such as the near infrared (NIR) wavelength range of approximately 800-2500 nm, 1500-2050 nm, or 1600-1800 nm. Estimations of formation fluid properties according to one or more aspects of the present disclosure may utilize optical data collected at a single wavelength, at multiple wavelengths, at a range of wavelengths, or at multiple wavelength ranges.

The spectrometer 672 may measure one or more optical characteristics of the formation fluid flowing through the flowline 670 and output optical spectra and/or other data representative of the detected optical characteristics. The optical characteristics may include OD of the formation fluid at each of the detected wavelengths or wavelength ranges. The OD is a logarithmic measurement relating the intensity of light emitted from the light source 692 to the intensity of light detected by the detector 694 at a certain wavelength or wavelength range. Each wavelength or range may correspond to a compositional component of the formation fluid. For example, each wavelength, wavelength range, or combination of wavelengths/ranges may pertain to a corresponding one of $CO_2$, C1, C2, C3, C4, C5, and C6+, although other arrangements are also within the scope of the present disclosure.

The spectrometer 672 may send optical spectra and/or other data representative of the measured optical characteristics to a processor 700 of the control/monitoring system 690. In the context of the present disclosure, the term "processor" refers to any number of processor components. The processor 700 may include a single processor disposed onboard the downhole tool 650. In other implementations, at least a portion of the processor 700 (e.g., where multiple processors collectively operate as the processor 700) may be located within the wellsite surface equipment 656 of FIG. 31, the logging and control unit 544 of FIG. 30, and/or other surface equipment components. The processor 700 may also or instead be or include one or more processors located within the downhole tool 650 and connected to one or more processors located in drilling and/or other equipment disposed at the wellsite surface 516. Moreover, various combinations of processors may be considered part of the processor 700 in the following discussion. Similar terminology is applied with respect to the control/monitoring system 690, as well as a memory 702 of the control/monitoring system 690, meaning that the control/monitoring system 690 may include various processors communicatively coupled to each other and/or various memories at various locations.

The control/monitoring system 690 may estimate the FVF, GOR, and/or other parameters of the formation fluid, as described above, based on the OD data received from the spectrometer 672, a density sensor, a pressure sensor, a temperature sensor, and/or other sensors, and may utilize the estimated FVF, GOR, and/or other parameters of the formation fluid to determine density, mass fractions of compositional components, OBM filtrate contamination, and/or other properties of the formation fluid. To make these and other determinations, the processor 700 may execute instructions stored in the memory 702.

The processor 700 may be communicatively coupled with one or more operator interfaces 706 and/or control devices 708. The operator interface 706 may include logs of predicted formation fluid properties that are accessible to an operator. The control device 708 may include one or more devices and/or portions thereof that receive control signals for operation based on the estimated properties of the formation fluid. Such control devices 708 may implement changes in depth of the downhole tool 650 within the wellbore 526, adjustments to the pumping pressure and/or rate of the pump 668, and/or other control functions, perhaps based on obtained, calculated, and/or estimated formation fluid properties as described above.

One or more functions and/or other aspects of the downhole tool 650 may also be applicable or readily adaptable to at least a portion of the downhole apparatus shown in FIG. 30. For example, one or more of the SWD tools, LWD modules 540, and/or MWD modules 542 shown in FIG. 30 and/or described above may have one or more functions and/or other aspects in common with a corresponding portion(s) of the downhole tool 650 shown in FIGS. 31 and 32.

Figure 33:
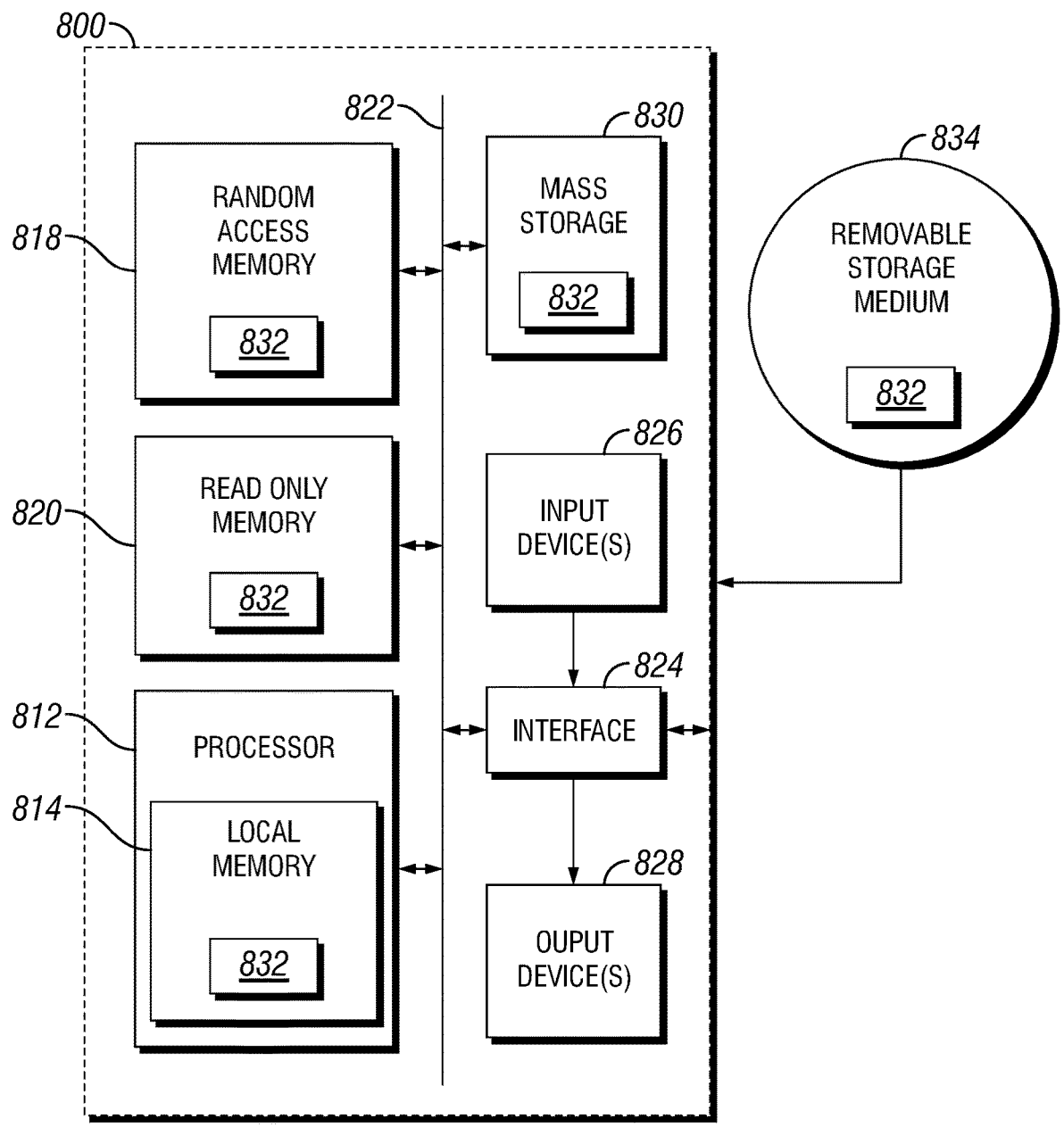
FIG. 33 is a schematic view of at least a portion of apparatus according to one or more aspects of the present disclosure.

FIG. 33 is a block diagram of an example processing system 800 that may execute example machine-readable instructions used to implement one or more of the workflows, methods, and/or processes described herein, and/or to implement a portion of one or more of the example downhole tools described herein.

The processing system 800 may be or comprise, for example, one or more processors, controllers, special-purpose computing devices, servers, personal computers, personal digital assistant (PDA) devices, smartphones, internet appliances, and/or other types of computing devices. Moreover, while it is possible that the entirety of the system 800 shown in FIG. 33 is implemented within a downhole tool, such as the downhole tools and/or modules shown in one or more of FIGS. 30-32, it is also contemplated that one or more components or functions of the system 800 may be implemented in wellsite surface equipment, perhaps including the logging and control unit 544 and/or other wellsite surface equipment depicted in FIG. 30 and/or the wellsite surface equipment 656 shown in FIG. 31.

The system 800 comprises a processor 812 such as, for example, a general-purpose programmable processor. The processor 812 includes a local memory 814, and executes coded instructions 832 present in the local memory 814 and/or in another memory device. The processor 812 may execute, among other things, machine-readable instructions to implement the methods and/or processes described herein. The processor 812 may be, comprise, or be implemented by various types of processing units, such as one or more INTEL microprocessors, microcontrollers from the ARM and/or PICO families of microcontrollers, embedded soft/hard processors in one or more FPGAs, etc. Of course, other processors from other families are also appropriate.

The processor 812 is in communication with a main memory including a volatile (e.g., random-access) memory 818 and a non-volatile (e.g., read-only) memory 820 via a bus 822. The volatile memory 818 may be, comprise, or be implemented by static random access memory (SRAM), synchronous dynamic random access memory (SDRAM), dynamic random access memory (DRAM), RAMBUS dynamic random access memory (RDRAM) and/or other types of random access memory devices. The non-volatile memory 820 may be, comprise, or be implemented by flash memory and/or other types of memory devices. One or more memory controllers (not shown) may control access to the memory 818 and/or 820.

The processing system 800 also includes an interface circuit 824. The interface circuit 824 may be, comprise, or be implemented by various types of standard interfaces, such as an Ethernet interface, a universal serial bus (USB), a third generation input/output (3GIO) interface, a wireless interface, and/or a cellular interface, among others. The interface circuit 824 may also comprise a graphics driver card. The interface circuit 824 may also include a communication device such as a modem or network interface card to facilitate exchange of data with external computers via a network (e.g., Ethernet connection, digital subscriber line (DSL), telephone line, coaxial cable, cellular telephone system, satellite, etc.).

One or more input devices 826 are connected to the interface circuit 824. The input device(s) 826 permit a user to enter data and commands into the processor 812. The input device(s) 826 may be, comprise, or be implemented by, for example, a keyboard, a mouse, a touchscreen, a track-pad, a trackball, an isopoint, and/or a voice recognition system, among others.

One or more output devices 828 are also connected to the interface circuit 824. The output devices 828 may be, comprise, or be implemented by, for example, display devices (e.g., a liquid crystal display or cathode ray tube display (CRT), among others), printers, and/or speakers, among others.

The processing system 800 also includes one or more mass storage devices 830 for storing machine-readable instructions and data. Examples of such mass storage devices 830 include floppy disk drives, hard drive disks, compact disk drives, and digital versatile disk (DVD) drives, among others. The coded instructions 832 may be stored in the mass storage device 830, the volatile memory 818, the non-volatile memory 820, the local memory 814, and/or on a removable storage medium, such as a CD or DVD 834.

As an alternative to implementing the methods and/or apparatus described herein in a system such as the processing system 800 of FIG. 33, methods and or apparatus within the scope of the present disclosure may be embedded in another structure, such as a processor and/or an application-specific integrated circuit (ASIC).

In view of the entirety of the present disclosure, including the claims and the figures, a person having ordinary skill in the art will readily recognize that the present disclosure introduces a method comprising: obtaining data associated with fluid obtained from a subterranean formation, wherein the obtained fluid is obtained from the subterranean formation via operation of a downhole sampling tool disposed proximate the subterranean formation in a wellbore extending from a wellsite surface into the subterranean formation, and wherein the obtained data is obtained via operation of at least one of the downhole sampling tool and surface equipment disposed at the wellsite surface and in communication with the downhole sampling tool; and via operation of at least one of the downhole sampling tool and the surface equipment: determining a start of linear behavior of a parameter in the obtained data, thus identifying linearly behaving data within the obtained data, wherein the linearly behaving data includes gas-oil ratio (GOR) data, density data, and optical density (OD) data; determining shrinkage factor based on the linearly behaving data; obtaining a first function relating the GOR data with the determined shrinkage factor; obtaining a second function relating the GOR data with the determined shrinkage factor; determining a first linear relationship between the OD data and one of the first and second functions; determining a second linear relationship between the density data and one of the first and second functions; determining at least one first fluid property of oil-based mud (OBM) filtrate contamination within the obtained fluid based on the first linear relationship; and determining at least one second fluid property of native formation fluid within the obtained fluid based on the second linear relationship.

Determining at least one first fluid property of OBM filtrate contamination within the obtained fluid based on the first linear relationship may comprise extrapolating the first linear relationship to determine at least one first fluid property of OBM filtrate contamination within the obtained fluid.

Determining at least one second fluid property of native formation fluid within the obtained fluid based on the second linear relationship may comprise extrapolating the second linear relationship to determine at least one second fluid property of native formation fluid within the obtained fluid.

One of the first and second functions relating the GOR data with the determined shrinkage factor may be $f=[GOR_0-(GOR_0-GOR)b]$, where $GOR_0$ is GOR of the native formation fluid within the obtained fluid, GOR is GOR of the obtained fluid, and b is the determined shrinkage factor.

One of the first and second functions relating the GOR data with the determined shrinkage factor may be $g=(GOR_0-GOR)b$, where $GOR_0$ is GOR of the native formation fluid within the obtained fluid, GOR is GOR of the obtained fluid, and b is the determined shrinkage factor.

The method may further comprise, via operation of at least one of the downhole sampling tool and the surface equipment, denoising the obtained data prior to identifying the linearly behaving data.

Determining shrinkage factor based on the linearly behaving data may comprise: determining formation volume factor (FVF) based on the linearly behaving data; and determining shrinkage factor based on the determined FVF. Such method may further comprise, via operation of at least one of the downhole sampling tool and the surface equipment, determining molecular weight of gas within the obtained fluid based on the linearly behaving data, wherein determining the FVF may be further based on the determined molecular weight of the gas. Such method may also or instead further comprise, via operation of at least one of the downhole sampling tool and the surface equipment, determining a stock tank oil (STO) basis density of the obtained fluid at standard conditions based on the linearly behaving data, wherein determining the FVF may be further based on the determined STO-basis density. Such method may also or instead further comprise, via operation of at least one of the downhole sampling tool and the surface equipment, estimating GOR of the native formation fluid based on the linearly behaving data, wherein determining the FVF may be further based on the estimated GOR.

The method may further comprise, via operation of at least one of the downhole sampling tool and the surface equipment: power law fitting the density data to the GOR data; and comparing first end points of the power law fitting with second end points of an extrapolation of the first or second functions.

The method may further comprise, via operation of at least one of the downhole sampling tool and the surface equipment, estimating a volume fraction of the OBM filtrate contamination within the obtained fluid based on the at least one first fluid property and the at least one second fluid property. Such method may further comprise, via operation of at least one of the downhole sampling tool and the surface equipment, converting the estimated volume fraction of the OBM filtrate contamination to an estimated weight fraction of the OBM filtrate contamination. Such method may further comprise, via operation of at least one of the downhole sampling tool and the surface equipment, converting the estimated volume fraction of the OBM filtrate contamination to an estimated weight fraction of the OBM filtrate contamination on a stock tank oil (STO) basis. Such methods may further comprise, via operation of at least one of the downhole sampling tool and the surface equipment, determining a composition of the native formation fluid based on the estimated volume fraction of the OBM filtrate contamination. Such methods may further comprise, via operation of at least one of the downhole sampling tool and the surface equipment, converting the estimated volume fraction of the OBM filtrate contamination from flowline conditions to formation conditions.

The estimated volume fraction of the OBM filtrate contamination within the obtained fluid may be a first estimated volume fraction, and the method may further comprise, via operation of at least one of the downhole sampling tool and the surface equipment: power law fitting the density data to the GOR data; determining a second estimated volume fraction of the OBM filtrate contamination within the obtained fluid based on the power law fitting; and determining uncertainty associated with each of the first and second estimated volume fractions. Such method may further comprise, via operation of at least one of the downhole sampling tool and the surface equipment, averaging or selecting the first and second estimated volume fractions based on the determined uncertainty.

The present disclosure also introduces a method comprising: obtaining data associated with fluid obtained from a subterranean formation, wherein the obtained fluid is obtained from the subterranean formation via operation of a downhole sampling tool disposed proximate the subterranean formation in a wellbore extending from a wellsite surface into the subterranean formation, wherein the obtained data is obtained via operation of at least one of the downhole sampling tool and surface equipment disposed at the wellsite surface and in communication with the downhole sampling tool, and wherein the obtained data includes gas-oil ratio (GOR) data; and via operation of at least one of the downhole sampling tool and the surface equipment: estimating a stock tank oil (STO) basis density of the obtained fluid based on the obtained data; fitting the estimated STO-basis density of the obtained fluid as a function of the GOR data to determine an STO-basis density of oil-based mud (OBM) filtrate contamination in the obtained fluid and a parameter relating the STO-basis density of the obtained fluid, the STO-basis density of the OBM filtrate contamination, and the GOR data; determining the STO-basis density of the obtained fluid based on the determined STO-basis density of the OBM filtrate contamination, the parameter, and the GOR data, thus obtaining a log of the STO-basis density of the obtained fluid with respect to volume of the obtained fluid or time elapsed during obtaining the obtained fluid; and determining an API gravity log based on the log of the STO-basis density of the obtained fluid.

The method may further comprise, via operation of at least one of the downhole sampling tool and the surface equipment, denoising the obtained data prior to estimating the STO-basis density of the obtained fluid.

The method may further comprise, via operation of at least one of the downhole sampling tool and the surface equipment: determining a molecular weight of gas within the obtained fluid based on the obtained data; estimating an initial formation volume factor (FVF) of the obtained fluid based on the log of the STO-basis density of the obtained fluid and the determined molecular weight of gas within the obtained fluid; fitting the initial FVF as a function of FVF of the OBM filtrate contamination, the GOR data, and a fitting parameter, thus obtaining a log of FVF of the obtained fluid with respect to volume of the obtained fluid or time elapsed during obtaining the obtained fluid; determining GOR of native formation fluid within the obtained fluid; and determining a final FVF of the obtained fluid based on the determined GOR of the native fluid and the fitting parameter.

Determining the GOR of the native fluid may comprise: determining shrinkage factor based on the determined final FVF of the obtained fluid; obtaining a function relating the GOR data with the determined shrinkage factor; determining a linear relationship between the function and either the density data or the OD data; and determining the GOR of the native fluid based on the linear relationship. In such implementations, the function may be selected from the group consisting of: $f=[GOR_0-(GOR_0-GOR)b]$; and $g=(GOR_0-GOR)b$; where $GOR_0$ is GOR of the native formation fluid within the obtained fluid, GOR is GOR of the obtained fluid, and b is the determined shrinkage factor.

The present disclosure also introduces a method comprising: obtaining data associated with fluid obtained from a subterranean formation, wherein the obtained fluid is obtained from the subterranean formation via operation of a downhole sampling tool disposed proximate the subterranean formation in a wellbore extending from a wellsite surface into the subterranean formation, wherein the obtained data is obtained via operation of at least one of the downhole sampling tool and surface equipment disposed at the wellsite surface and in communication with the downhole sampling tool, and wherein the obtained data includes gas-oil ratio (GOR) data and formation volume factor (FVF) data; and via operation of at least one of the downhole sampling tool and the surface equipment: determining a linear relation between the FVF data and the GOR data; determining the slope of the linear relation; obtaining GOR and density of the native formation fluid within the obtained fluid; determining stock tank oil (STO) basis density of native formation fluid within the obtained fluid based on the slope of the linear relation, GOR of the native formation fluid, and density of the native formation fluid; determining a parameter relating STO-basis density of the native formation fluid, STO-basis density of oil-based mud (OBM) filtrate contamination within the obtained fluid, and GOR of the native formation fluid; and determining STO-basis density of the obtained fluid based on the STO-basis density of OBM filtrate contamination, the parameter, and the GOR data.

The method may further comprise, via operation of at least one of the downhole sampling tool and the surface equipment, determining API gravity of the obtained fluid based on the STO-basis density of the obtained fluid.

Obtaining GOR and density of the native formation fluid may comprise: determining a start of linear behavior of a parameter in the obtained data, thus identifying linearly behaving data within the obtained data; determining shrinkage factor based on the linearly behaving data; obtaining one or more functions relating the GOR data with the determined shrinkage factor; determining GOR of the native formation fluid based on at least one of the one or more functions; determining a linear relationship between the density data and one of the one or more functions; and determining density of the native formation fluid based on the linear relationship. In such implementations, each of the one or more functions may be selected from the group consisting of: $f=[GOR_0-(GOR_0-GOR)b]$; and $g=(GOR_0-GOR)b$; where $GOR_0$ is GOR of the native formation fluid within the obtained fluid, GOR is GOR of the obtained fluid, and b is the determined shrinkage factor.

The foregoing outlines features of several embodiments so that a person having ordinary skill in the art may better understand the aspects of the present disclosure. A person having ordinary skill in the art should appreciate that they may readily use the present disclosure as a basis for designing or modifying other processes and structures for carrying out the same functions and/or achieving the same benefits of the embodiments introduced herein. A person having ordinary skill in the art should also realize that such equivalent constructions do not depart from the spirit and scope of the present disclosure, and that they may make various changes, substitutions and alterations herein without departing from the spirit and scope of the present disclosure.

The Abstract at the end of this disclosure is provided to comply with 37 C.F.R. § 1.72(b) to permit the reader to quickly ascertain the nature of the technical disclosure. It is submitted with the understanding that it will not be used to interpret or limit the scope or meaning of the claims.

What is claimed is:

1. A method, comprising:
obtaining data associated with a fluid obtained from a subterranean formation via operation of a downhole sampling tool disposed proximate the subterranean formation in a wellbore extending from a wellsite surface into the subterranean formation;
estimating a stock tank oil (STO) basis density of a fluid obtained from the subterranean formation based on the data associated with the obtained fluid, wherein the data includes gas-oil ratio (GOR) data;
fitting the estimated STO-basis density of the obtained fluid as a function of the GOR data to determine an STO-basis density of oil-based mud (OBM) filtrate contamination in the obtained fluid and a parameter relating the STO-basis density of the obtained fluid, the STO-basis density of the OBM filtrate contamination, and the GOR data;
determining the STO-basis density of the obtained fluid based on the determined STO-basis density of the OBM filtrate contamination, the parameter, and the GOR data, thus obtaining a log of the STO-basis density of the obtained fluid with respect to volume of the obtained fluid or time elapsed during obtaining the obtained fluid;
determining an American Petroleum Institute (API) gravity log based on the log of the STO-basis density of the obtained fluid; and
estimating a volume fraction of OBM filtrate contamination within the obtained fluid based on the API gravity log.

2. The method of claim 1, wherein obtaining the data comprises operation of the downhole sampling tool, or surface equipment disposed at the wellsite surface in communication with the downhole sampling tool, or both.

3. The method of claim 1 comprising:
determining a molecular weight of gas within the obtained fluid based on the obtained data;
estimating an initial formation volume factor (FVF) of the obtained fluid based on the log of the STO-basis density of the obtained fluid and the determined molecular weight of gas within the obtained fluid;
fitting the initial FVF as a function of FVF of the OBM filtrate contamination, the GOR data, and a fitting parameter, thus obtaining a log of FVF of the obtained fluid with respect to volume of the obtained fluid or time elapsed during obtaining the obtained fluid;
determining GOR of native formation fluid within the obtained fluid; and
determining a final FVF of the obtained fluid based on the determined GOR of the native fluid and the fitting parameter.

4. The method of claim 3 wherein determining the GOR of the native formation fluid comprises:
determining shrinkage factor based on the determined final FVF of the obtained fluid;
obtaining a function relating the GOR data with the determined shrinkage factor;
determining a linear relationship between the function and either the density data or the optical density (OD) data; and
determining the GOR of the native fluid based on the linear relationship.

5. The method of claim 1, comprising:
determining a linear relation between formation volume factor (FVF) data of the fluid obtained from the subterranean formation and gas-oil ratio (GOR) data of the fluid, wherein the data associated with the obtained fluid includes the FVF data and GOR data;
wherein the stock tank oil (STO) basis density of native formation fluid within the obtained fluid is determined based on a slope of the linear relation, the GOR of the native formation fluid, and a density of the native formation fluid;
determining a parameter relating STO-basis density of the native formation fluid, STO-basis density of oil-based mud (OBM) filtrate contamination within the obtained fluid, and GOR of the native formation fluid; and
determining STO-basis density of the obtained fluid based on the STO-basis density of OBM filtrate contamination, the parameter, and the GOR data.

6. The method of claim 5, comprising obtaining the data via operation of a downhole sampling tool disposed proximate the subterranean formation in a wellbore extending from a wellsite surface into the subterranean formation, wherein the data is obtained via operation of the downhole sampling tool, or surface equipment disposed at the wellsite surface in communication with the downhole sampling tool, or both.

7. The method of claim 5 comprising determining API gravity of the obtained fluid based on the STO-basis density of the obtained fluid.

8. An article of manufacture comprising one or more tangible, non-transitory, machine-readable media comprising instructions that, when executed by a processor, cause the processor to:
retrieve data associated with a fluid obtained from a subterranean formation via operation of a downhole sampling tool disposed proximate the subterranean formation in a wellbore extending from a wellsite surface into the subterranean formation;
estimate a stock tank oil (STO) basis density of the fluid obtained from the subterranean formation based on the data associated with the obtained fluid, wherein the data includes gas-oil ratio (GOR) data;
fit the estimated STO-basis density of the obtained fluid as a function of the GOR data to determine an STO-basis density of oil-based mud (OBM) filtrate contamination in the obtained fluid and a parameter relating the STO-basis density of the obtained fluid, the STO-basis density of the OBM filtrate contamination, and the GOR data;
determine the STO-basis density of the obtained fluid based on the determined STO-basis density of the OBM filtrate contamination, the parameter, and the GOR data, thus obtaining a log of the STO-basis density of the obtained fluid with respect to volume of the obtained fluid or time elapsed during obtaining the obtained fluid;
determine an American Petroleum Institute (API) gravity log based on the log of the STO-basis density of the obtained fluid; and
estimate a volume fraction of OBM filtrate contamination within the obtained fluid based on the API gravity log.

9. The article of manufacture of claim 8, wherein the instructions comprise instructions that, when executed by the processor, cause the processor to:
determine a molecular weight of gas within the obtained fluid based on the obtained data;
estimate an initial formation volume factor (FVF) of the obtained fluid based on the log of the STO-basis density of the obtained fluid and the determined molecular weight of gas within the obtained fluid;

fit the initial FVF as a function of FVF of the OBM filtrate contamination, the GOR data, and a fitting parameter, thus obtaining a log of FVF of the obtained fluid with respect to volume of the obtained fluid or time elapsed during obtaining the obtained fluid;

determine GOR of native formation fluid within the obtained fluid; and determine a final FVF of the obtained fluid based on the determined GOR of the native fluid and the fitting parameter.

10. The article of manufacture of claim 9, wherein the instructions to determine the GOR of the native formation fluid comprise instructions to:

determine shrinkage factor based on the determined final FVF of the obtained fluid;

obtain a function relating the GOR data with the determined shrinkage factor;

determine a linear relationship between the function and either the density data or the optical density (OD) data; and determine the GOR of the native fluid based on the linear relationship.

11. A system comprising:

a downhole sampling tool configured to obtain a fluid from a subterranean formation; and a data processing system comprising a processor configured to:

estimate a stock tank oil (STO) basis density of the fluid obtained from the subterranean formation based on the data associated with the obtained fluid, wherein the data includes gas-oil ratio (GOR) data;

fit the estimated STO-basis density of the obtained fluid as a function of the GOR data to determine an STO-basis density of oil-based mud (OBM) filtrate contamination in the obtained fluid and a parameter relating the STO-basis density of the obtained fluid, the STO-basis density of the OBM filtrate contamination, and the GOR data;

determine the STO-basis density of the obtained fluid based on the determined STO-basis density of the OBM filtrate contamination, the parameter, and the GOR data, thus obtaining a log of the STO-basis density of the obtained fluid with respect to volume of the obtained fluid or time elapsed during obtaining the obtained fluid;

determine an American Petroleum Institute (API) gravity log based on the log of the STO-basis density of the obtained fluid; and estimate a volume fraction of OBM filtrate contamination within the obtained fluid based on the API gravity log.

12. The system of claim 11, wherein the processor is configured to:

determine a molecular weight of gas within the obtained fluid based on the obtained data;

estimate an initial formation volume factor (FVF) of the obtained fluid based on the log of the STO-basis density of the obtained fluid and the determined molecular weight of gas within the obtained fluid;

fit the initial FVF as a function of FVF of the OBM filtrate contamination, the GOR data, and a fitting parameter, thus obtaining a log of FVF of the obtained fluid with respect to volume of the obtained fluid or time elapsed during obtaining the obtained fluid;

determine GOR of native formation fluid within the obtained fluid; and determine a final FVF of the obtained fluid based on the determined GOR of the native fluid and the fitting parameter.

13. The system of claim 12, wherein the processor is configured to determine the GOR of the native formation fluid at least partly by:

determining shrinkage factor based on the determined final FVF of the obtained fluid;

obtaining a function relating the GOR data with the determined shrinkage factor;

determining a linear relationship between the function and either the density data or the optical density (OD) data; and determining the GOR of the native fluid based on the linear relationship.

* * * * *